(12) United States Patent
Sarem et al.

(10) Patent No.: US 6,576,458 B1
(45) Date of Patent: Jun. 10, 2003

(54) CELL AND TISSUE CULTURE DEVICE WITH CONTROLLED CULTURE FLUID FLOW

(75) Inventors: Farzin Sarem, 19 rue du Morvan, 54500 Vandoeuvre-les-Nancy (FR); Leila-Ouassila Sarem Damerdji, Vandoeuvre-les-Nancy (FR)

(73) Assignee: Farzin Sarem, Vandoeuvre-les-Nancy (FR)

( * ) Notice: Subject to any disclaimer, the term of this patent is extended or adjusted under 35 U.S.C. 154(b) by 243 days.

(21) Appl. No.: 09/665,692

(22) Filed: Sep. 20, 2000

(30) Foreign Application Priority Data

Jan. 17, 2000 (FR) .............................................. 00 00547

(51) Int. Cl.⁷ ................................................ C12M 1/36
(52) U.S. Cl. ................................ 435/286.5; 435/286.6; 435/297.1; 435/297.5
(58) Field of Search ..................... 435/286.1, 286.5, 435/286.6, 297.1, 297.5

(56) References Cited

U.S. PATENT DOCUMENTS 4,647,539 A * 3/1987 Bach ..................... 210/321.67
5,707,868 A 1/1998 Boulay et al. ............... 435/383
6,037,141 A * 3/2000 Banes ....................... 435/286.6

FOREIGN PATENT DOCUMENTS

WO WO 96/12789 5/1996

* cited by examiner

Primary Examiner—David A. Redding
(74) Attorney, Agent, or Firm—Young & Thompson

(57) ABSTRACT

A cell and tissue culture device comprises a closed pressurization circuit (2) able to deliver a selected gas under a selected pressure, at least a culture chamber (6) accommodating means (13) for supporting at least a deformable membrane (14) forming in chamber (6) an interface between first (17) and second (16) portions with variable complementary volumes, wherein the first portion (17) is configured for receiving cells and/or tissues to be grown for being supplied with culture fluid by a first tank (8), and said second portion (16) is configured for being supplied with gas by the pressurization circuit (2) and for discharging at least a portion of this gas. In addition, it comprises control means (3,4) capable of determining, according to selected criteria relating to the type of culture to be achieved, the gas to be fed into the second portion (16), its pressure and the time for feeding in this gas, and of controlling access to the first and second portions of the chamber (6) so as to control together the shape of the membrane (14), the culture fluid supply and the flow of this fluid in the first portion.

59 Claims, 11 Drawing Sheets

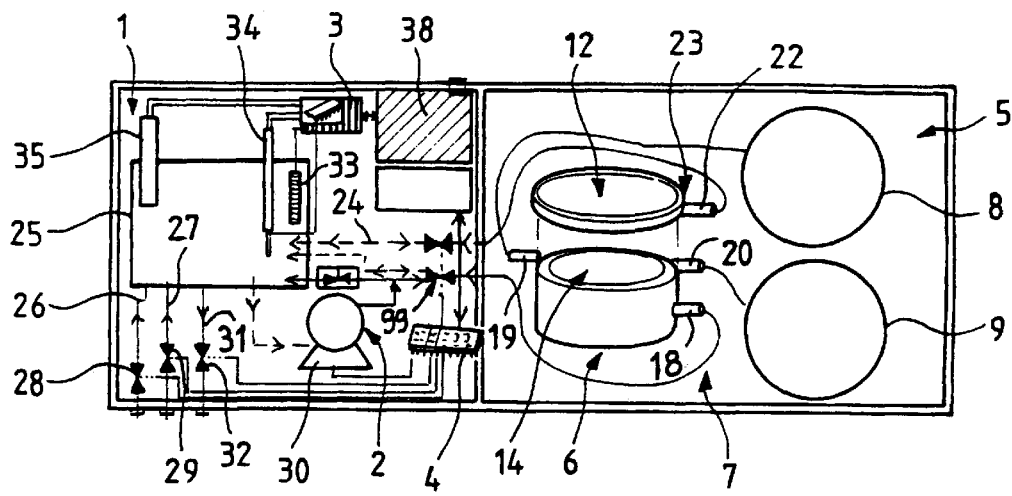
FIG_1
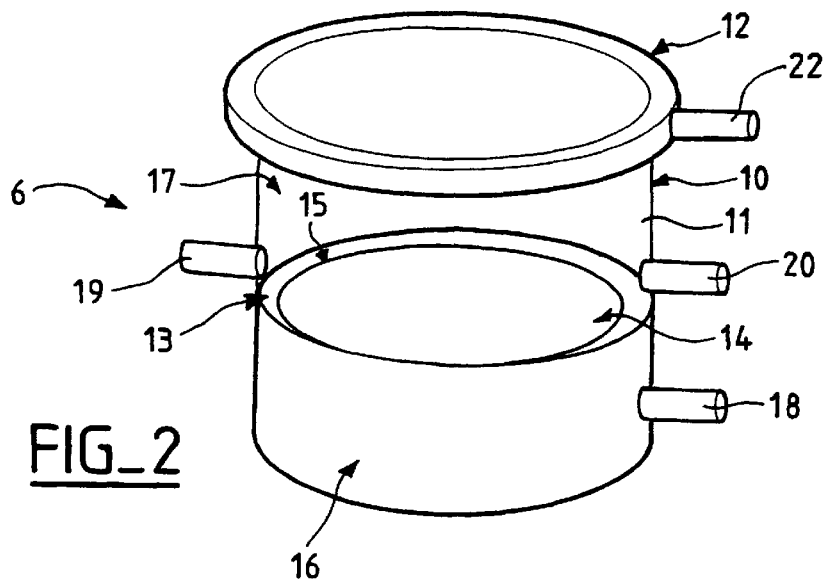
FIG_2
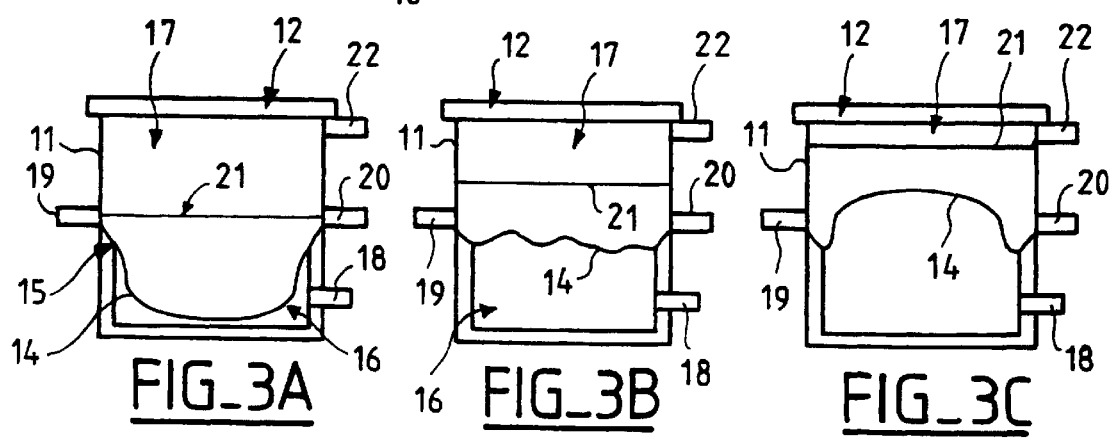
FIG_3A  FIG_3B  FIG_3C

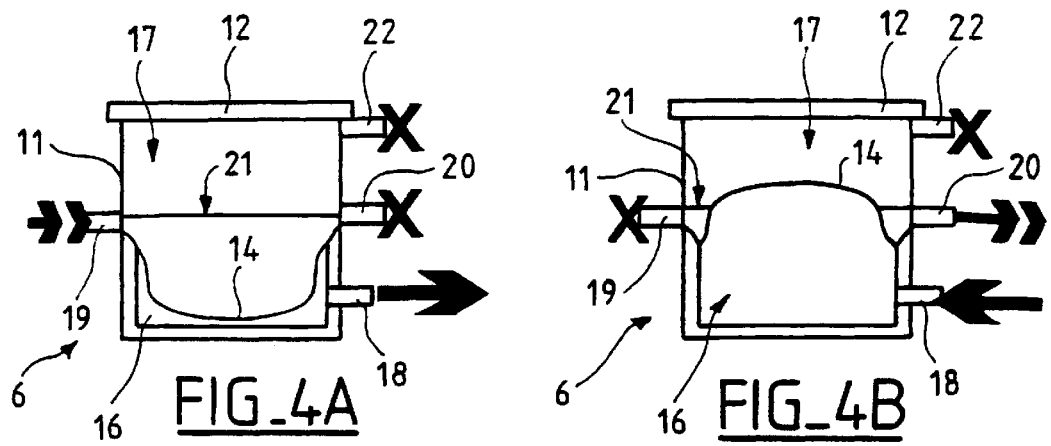
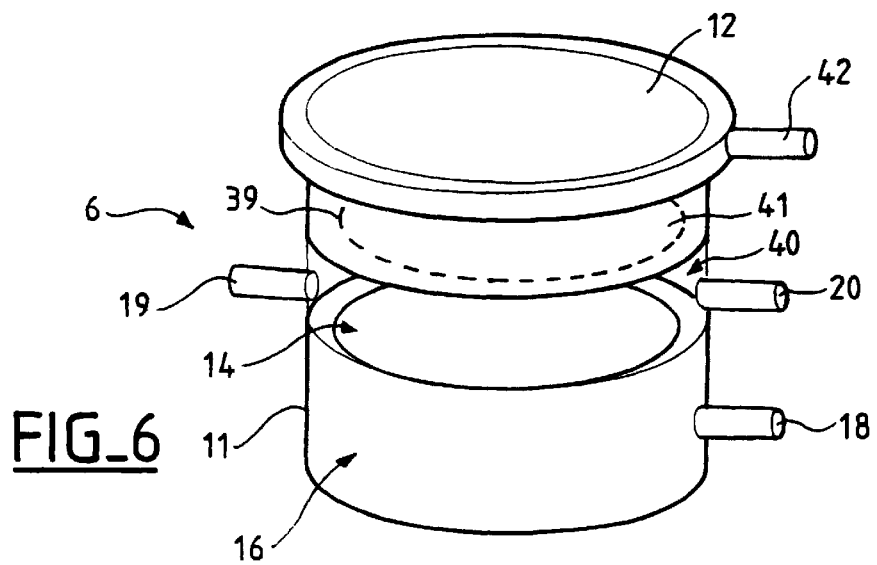
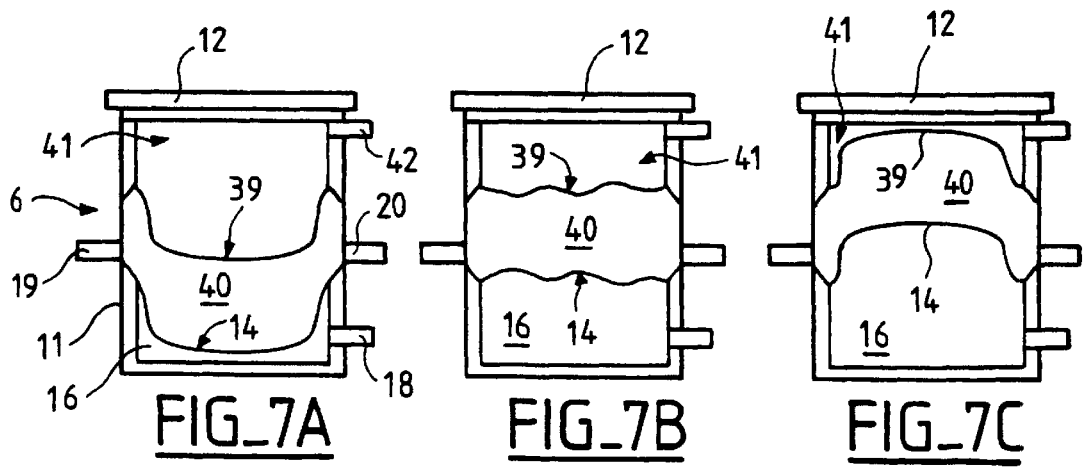

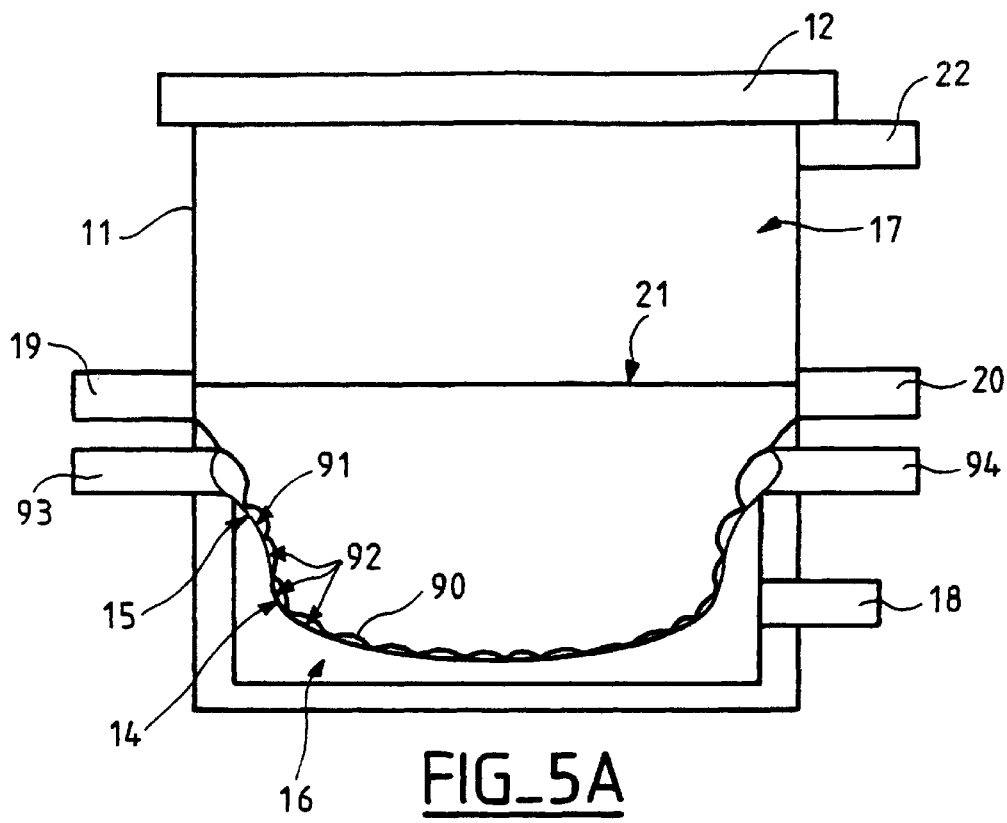
FIG_5A
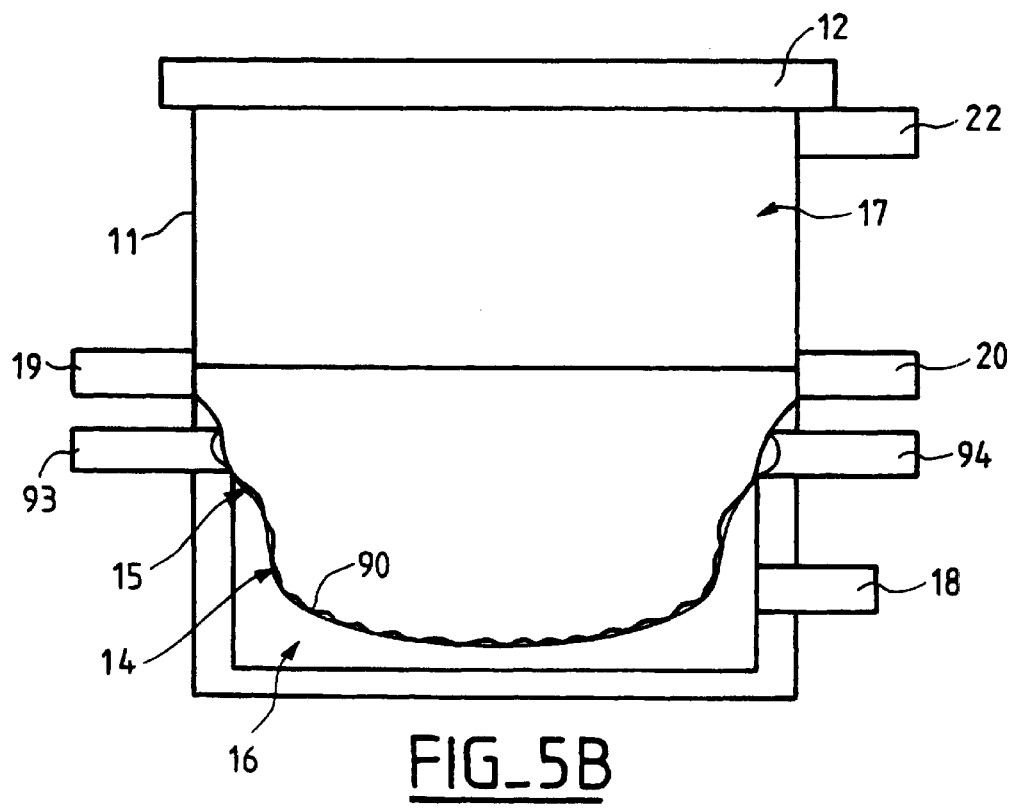
FIG_5B

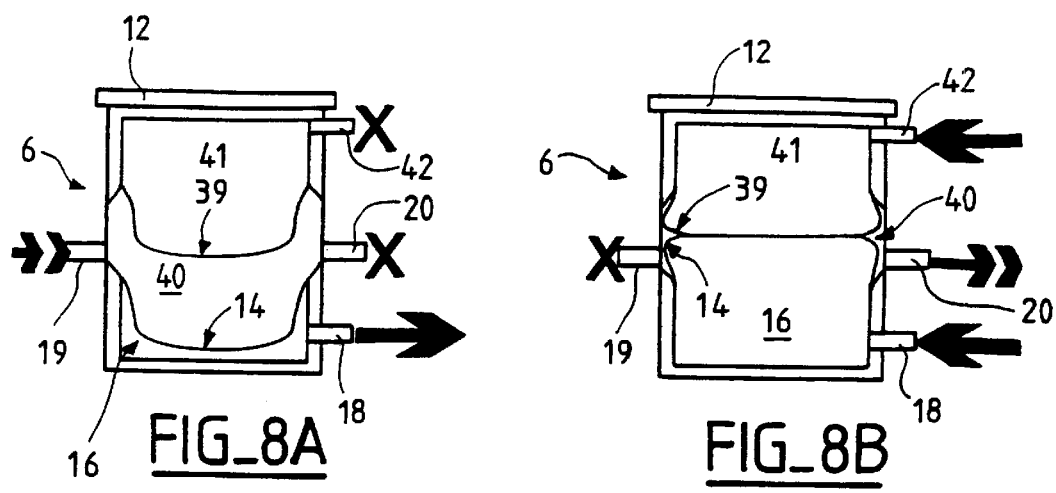
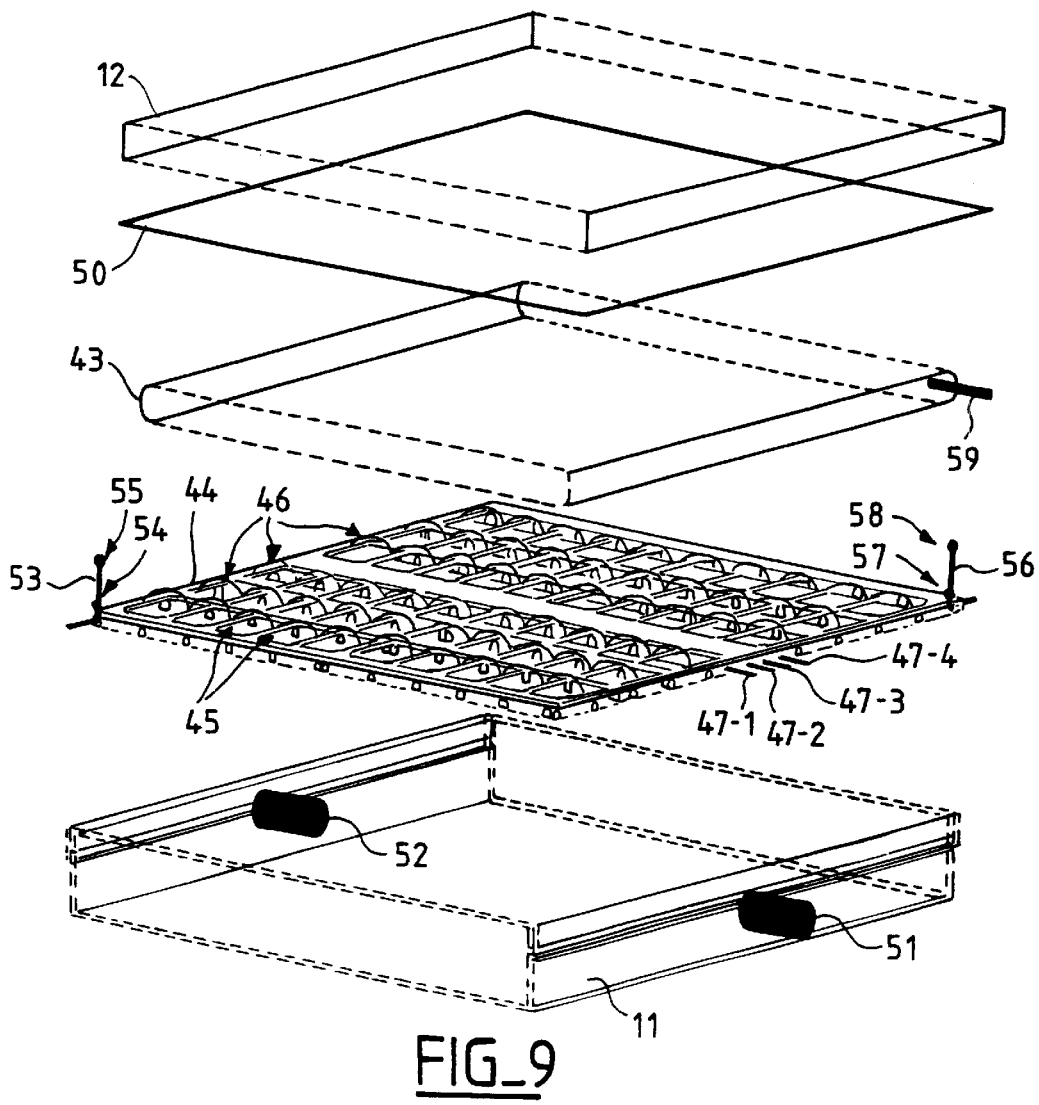

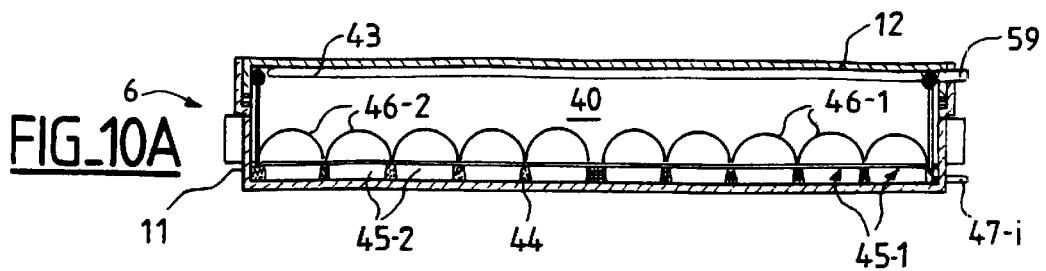
FIG_10A
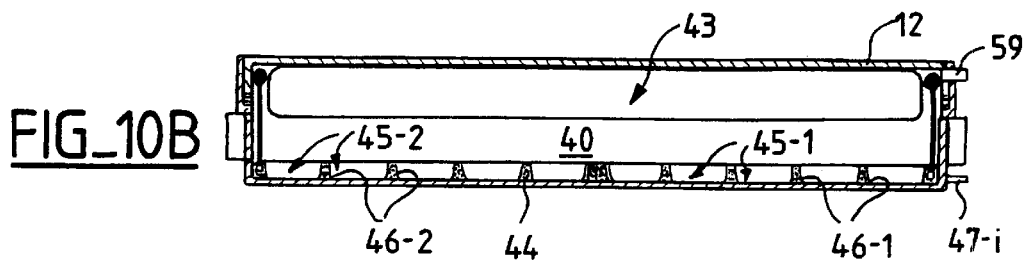
FIG_10B
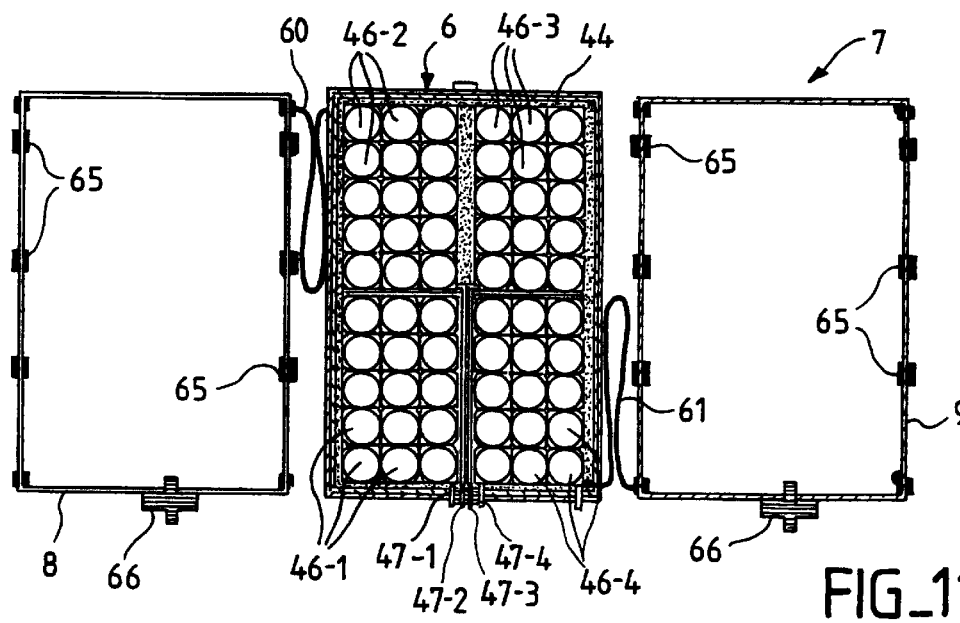
FIG_11A
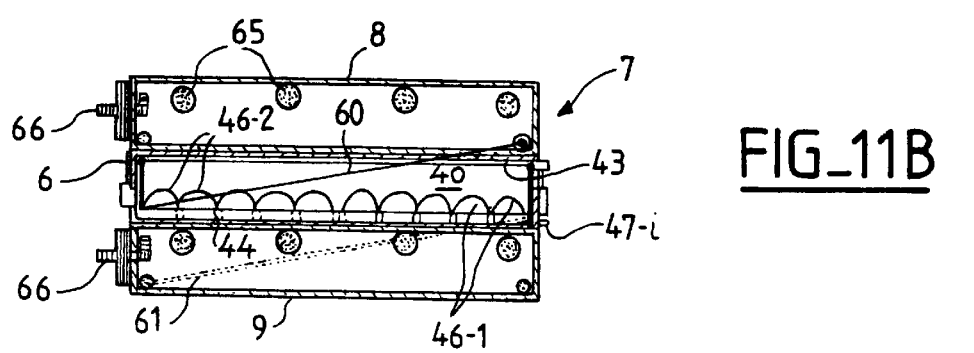
FIG_11B

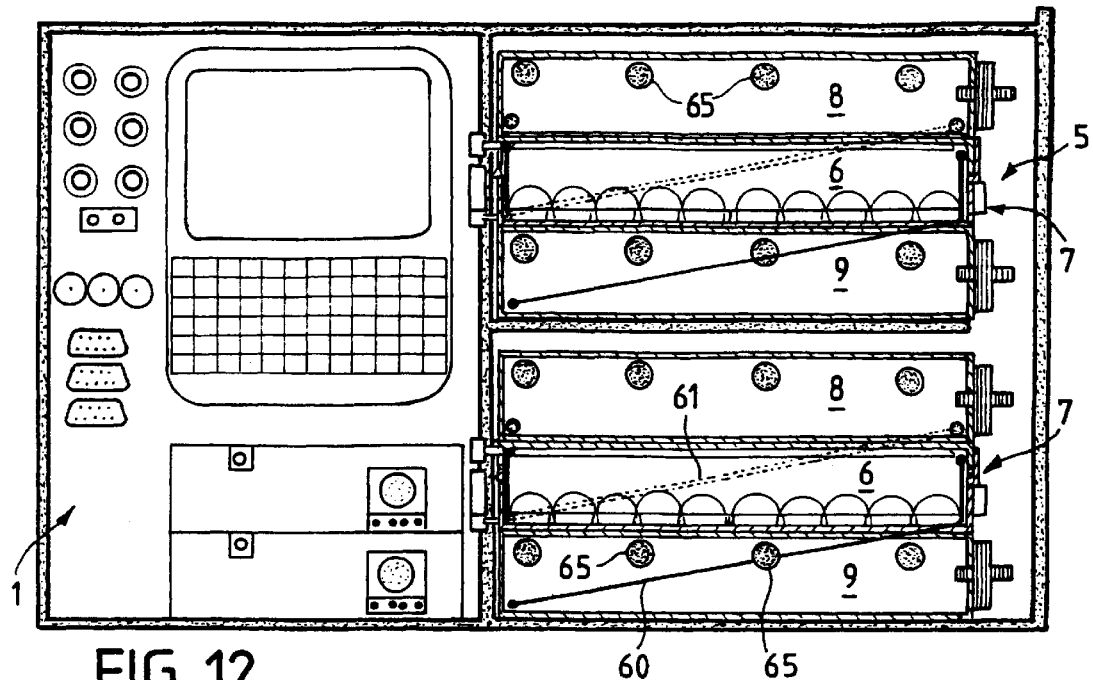
FIG_12
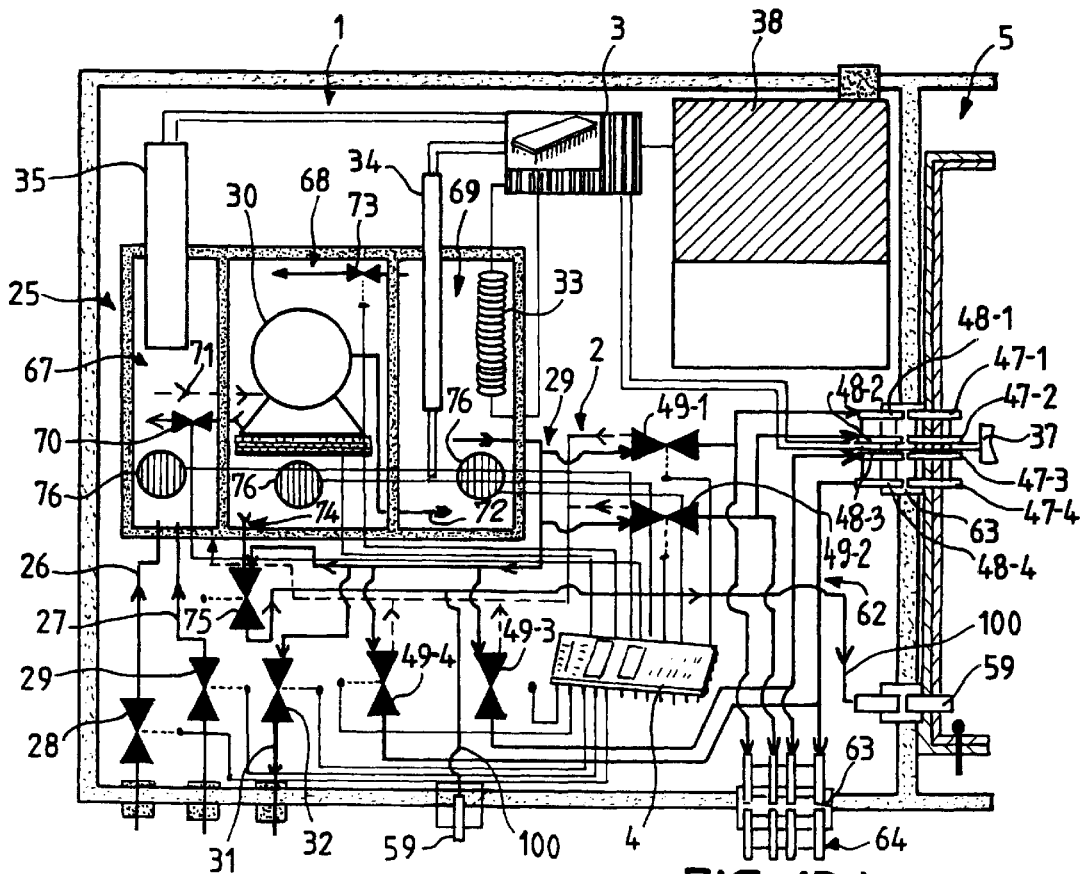
FIG_13A

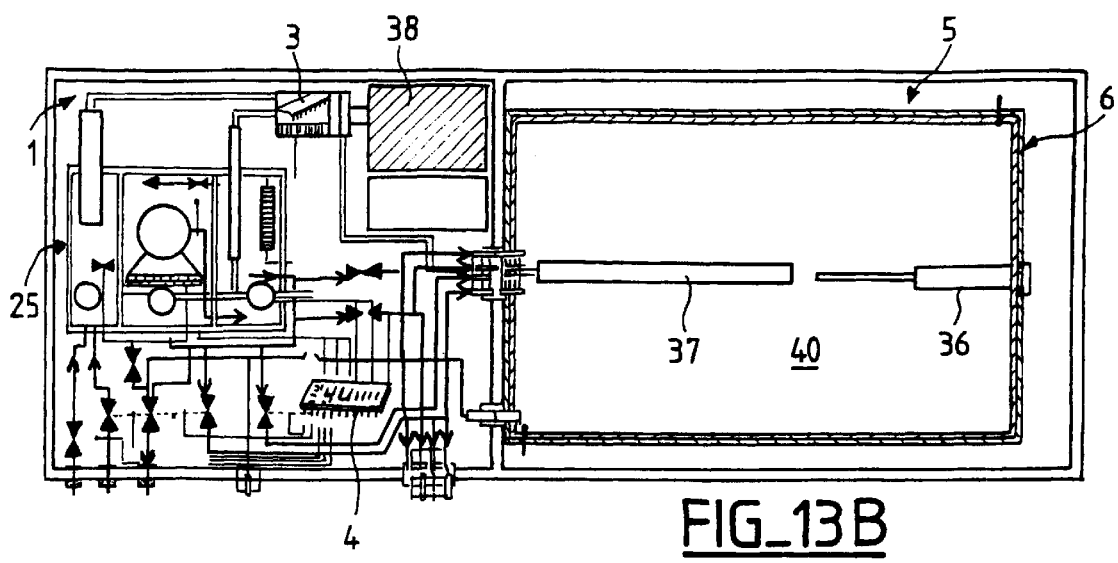
FIG_13B
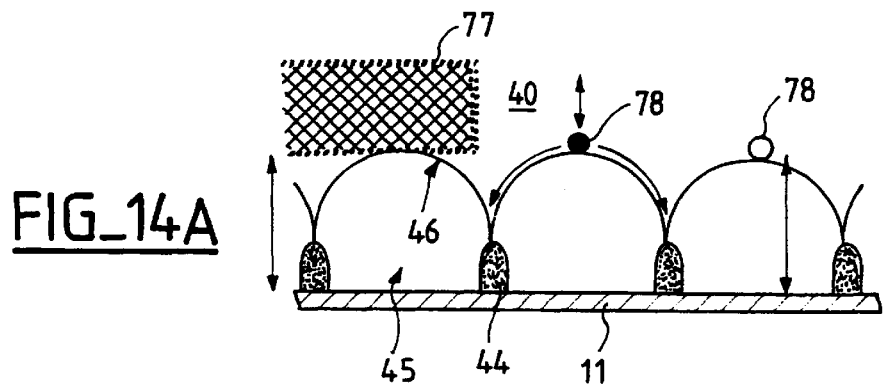
FIG_14A
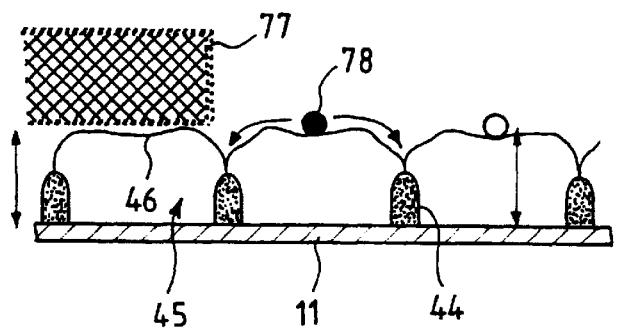
FIG_14B
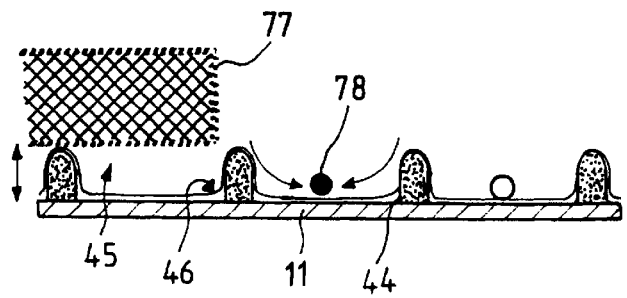
FIG_14C

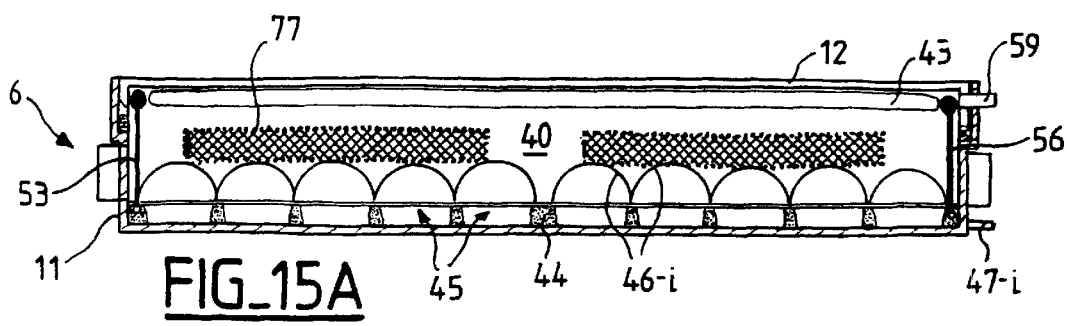
FIG_15A
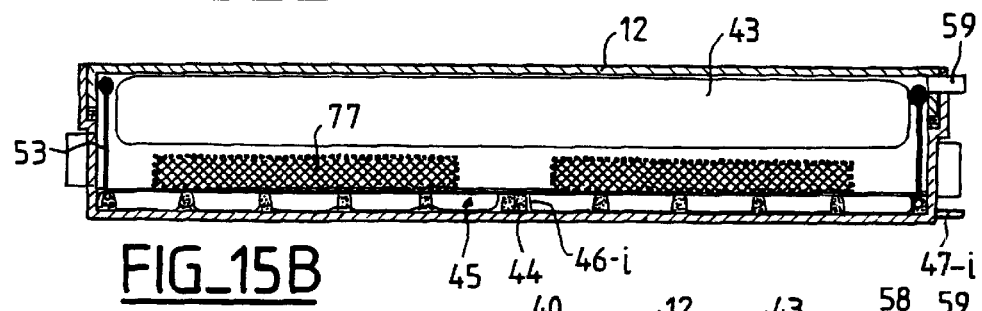
FIG_15B
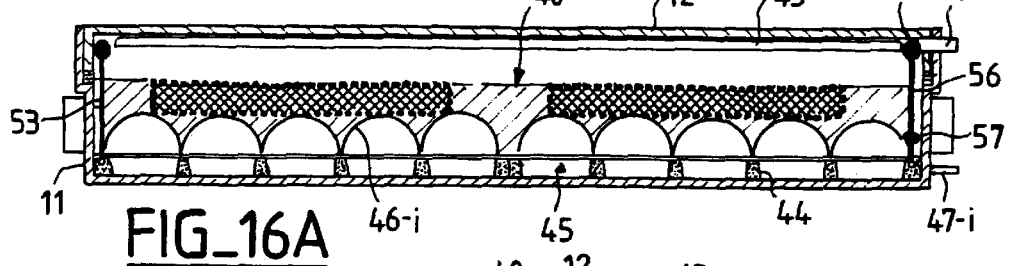
FIG_16A
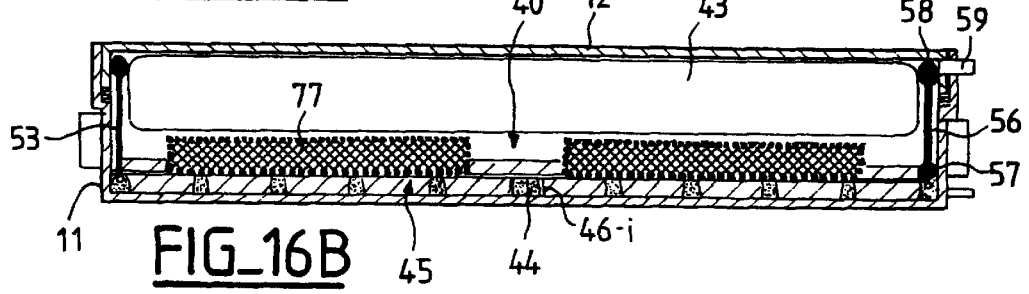
FIG_16B
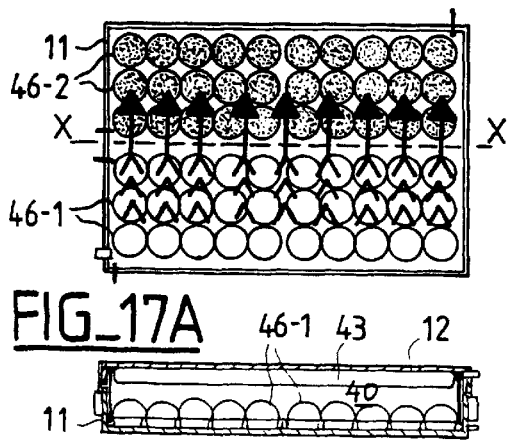
FIG_17A
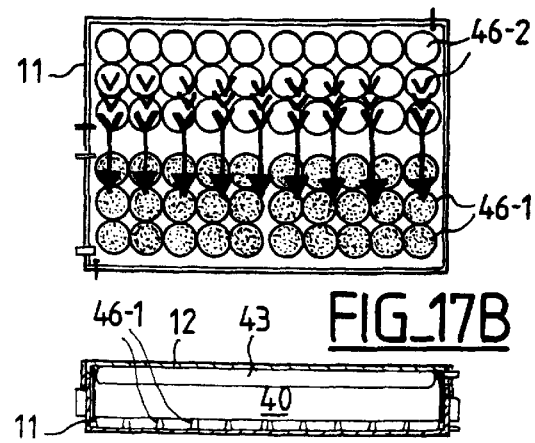
FIG_17B

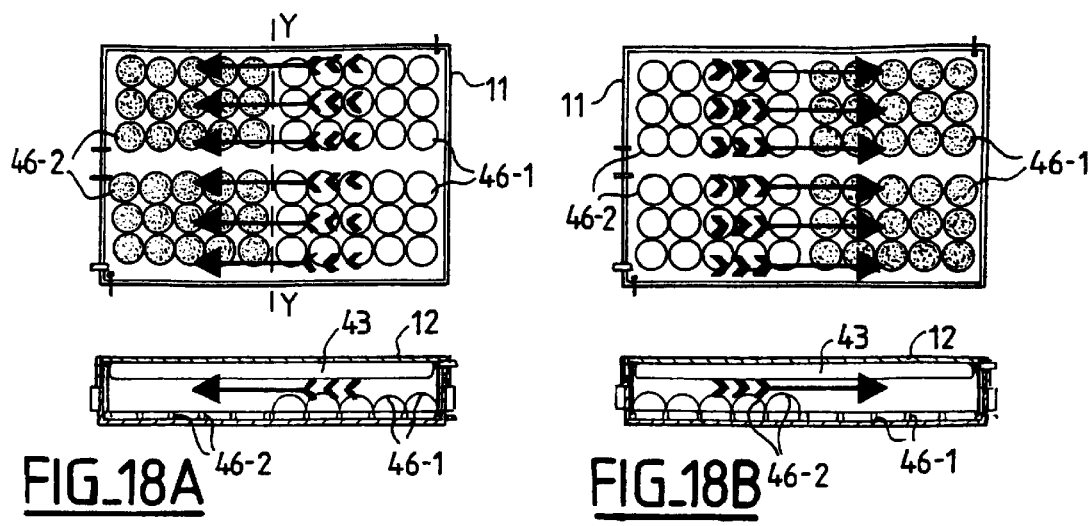
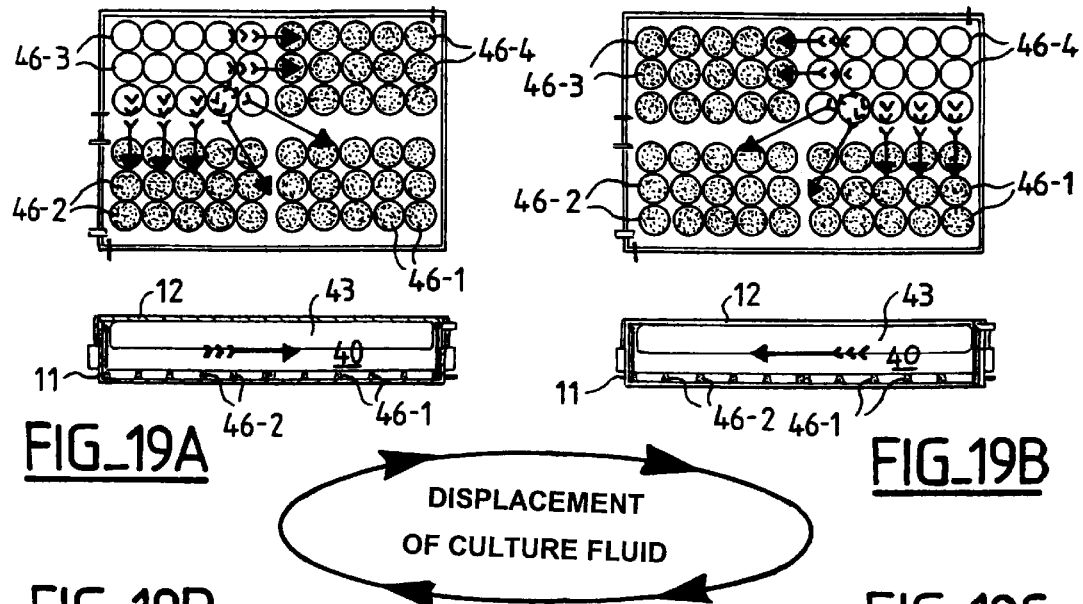
DISPLACEMENT OF CULTURE FLUID
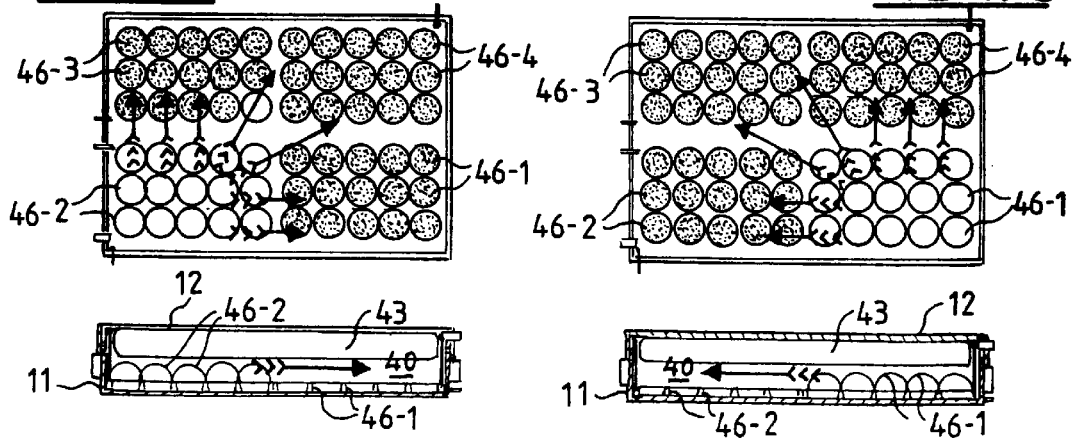

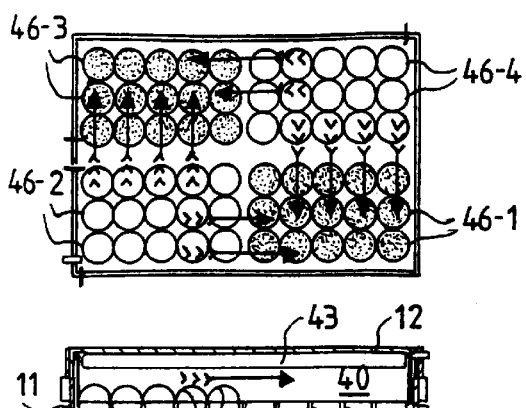
FIG_20A
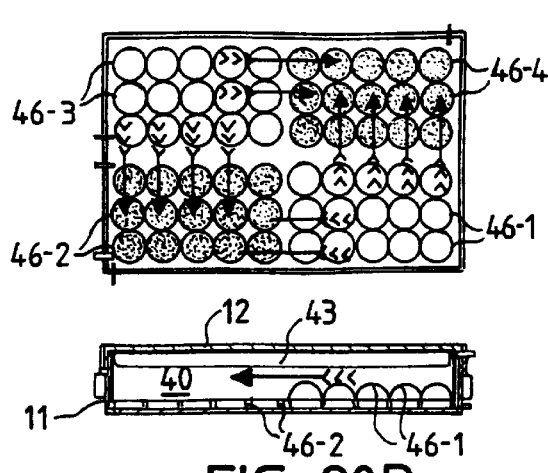
FIG_20B
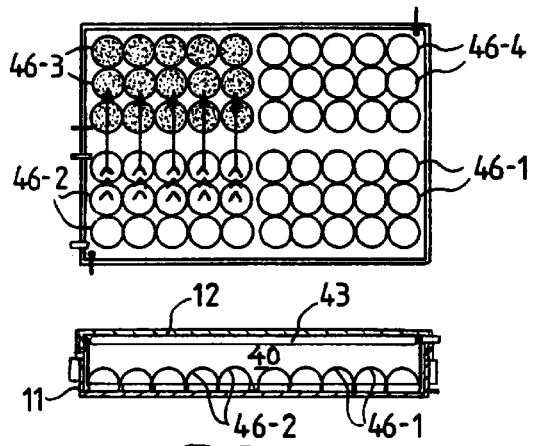
FIG_21A
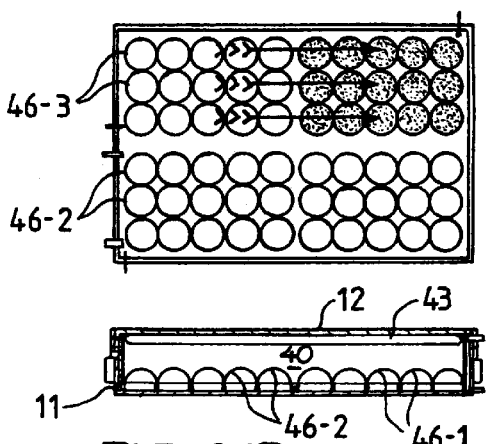
FIG_21B
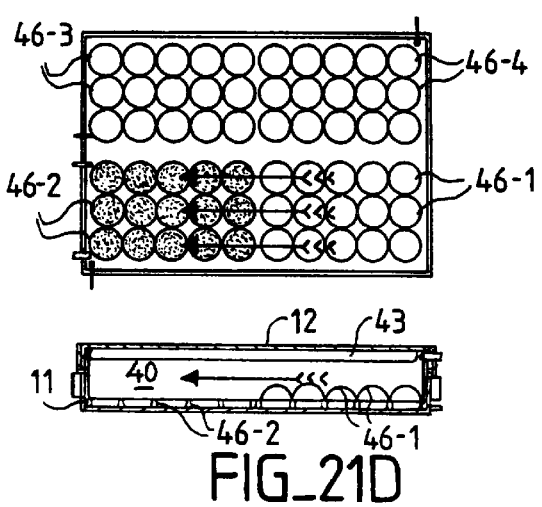
FIG_21D
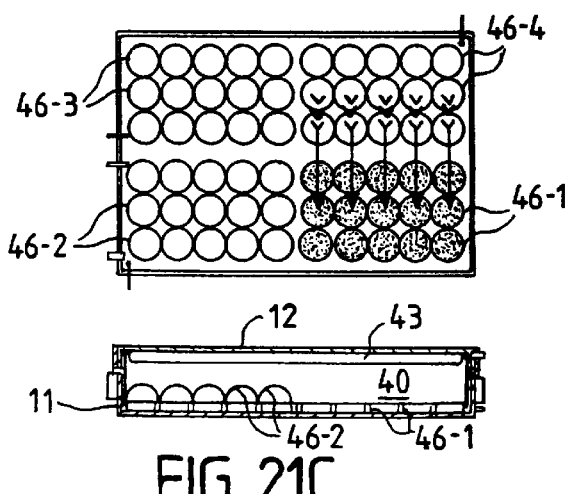
FIG_21C

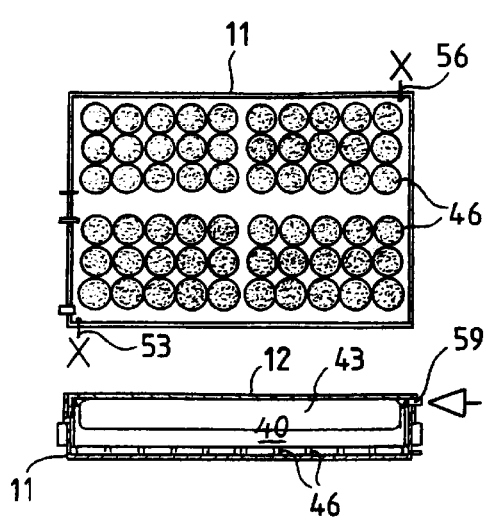
FIG_22A
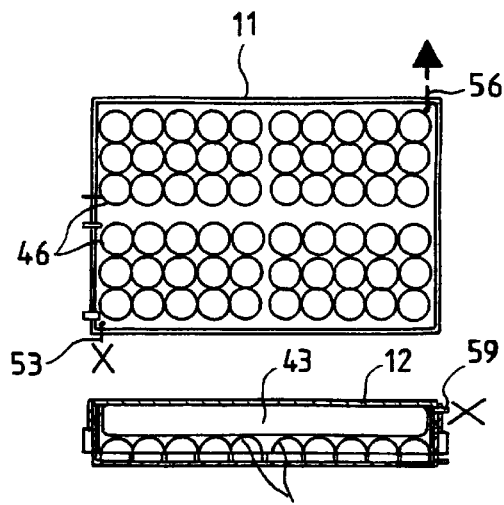
FIG_22B
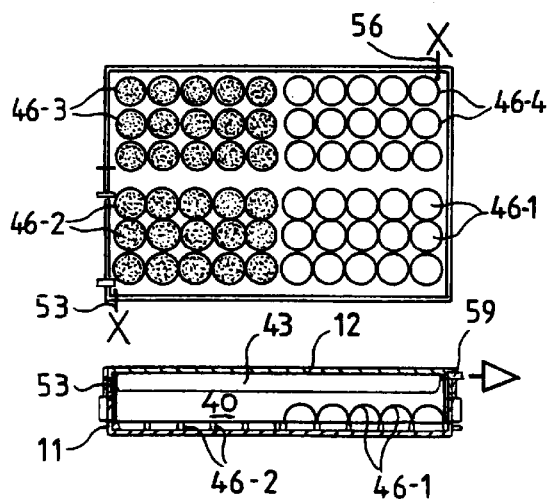
FIG_23A
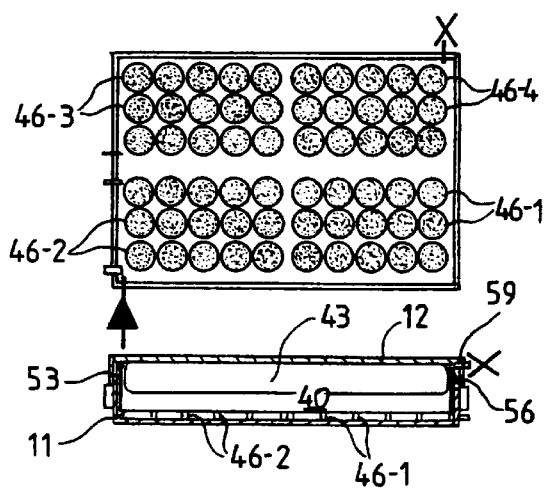
FIG_23B

CELL AND TISSUE CULTURE DEVICE WITH CONTROLLED CULTURE FLUID FLOW

The invention relates to the field of cell and tissue culture with the help of a culture fluid or nutrient medium.

This invention more particularly relates to devices and methods for cell and tissue culture in which the culture fluid (or nutrient) is set into motion so as to achieve a dynamic culture. Such devices usually apply either a technique for directly stirring the culture fluid in the culture volume or a technique providing permanent flow of the fluid through a specific circuit.

These techniques for fluid flow are difficult to control because culture conditions change over time. Actually, the low cell concentration which exists at the beginning of the culture process, requires a quasi-static environment, and therefore a very low culture fluid flow rate, whereas cell multiplication or tissue growth needs a rapidly increasing flow rate.

Maintaining adequate conditions during the whole culture process requires either the use of several suitable devices, at different stages of the culture's growth, respectively, and this involves many handling operations, or complex and often cumbersome means, which limit, even precludes observation of the culture's development with a microscope. These handling operations and means are all the more complex as the culture process should be carried out in a sterile environment which requires highly qualified personnel, and this therefore increases the cost for each culture. Furthermore, because of their price, these devices should be reusable, which imposes complete sterilization before each new culture, and maintenance operations.

The object of the invention is therefore to overcome all or part of the aforementioned drawbacks.

For this purpose, it provides a cell and tissue culture device which initially comprises a pressurization circuit capable of delivering at least a selected gas under a selected pressure, at least a culture chamber accommodating supporting means for at least a deformable membrane forming inside the chamber an interface between first and second portions with variable complementary volumes and supplied with culture fluid by a first tank and with selected gas by the pressurization circuit, respectively; the first portion further receiving the cells or tissues to be grown. The device further comprises control means capable of determining, according to selected criteria relating to the type of culture to be achieved, the gas to be fed into the second portion, its pressure and the time for feeding it in, and of controlling access to the first and second portions of the chamber so as to control together the shape of the membrane, culture fluid supply and flow of this fluid in the first portion.

By varying the pressure of the gas in the second portion, the shape of the membrane(s) may be changed, and the culture fluid may be forced to flow in the first portion of the chamber. For example, overpressurization phases may be alternated with depressurization phases in the second portion of the chamber in order to cause oscillation of the membrane (s).

Thus, for example, defining for each type of culture, a series of parameter n-tuples each including at least a selected gas, a pressure for this gas, a time for feeding in this gas, a culture fluid flow rate and a time for feeding in this fluid, is sufficient for controlling the growth of this culture. However, more complex modes may be considered which are based on adapting the multiple parameters from physical measurements, such as temperature measurements, or measurements of the proportion of molecular species or even pH measurements, carried out in the chamber and/or in the pressurization circuit.

All these parameters may be stored and/or calculated in the control means. They may be also changed through reprogramming.

Conducting pressure measurements in the culture chamber, or measurements of culture fluid level in the culture chamber or even calorimetric measurements for quantifying growth of certain cultures, or even redox potential measurements may also be considered.

In the case of a single membrane device, providing a supramembrane above the latter may be advantageous, in order to delimit between them at least an intermediate area supplied with gas by the pressurization circuit and able to discharge at least a portion of this gas, wherein the control means are configured so as to determine, according to selected criteria, the gas to be fed into the intermediate area, its pressure and time for feeding it in, and for controlling access to the inlet and outlet of the intermediate area so as to control together the shapes of the membrane and supramembrane and culture fluid flow in the first portion. This supramembrane may be firmly secured to the membrane at a multiplicity of selected locations, so as to subdivide the intermediate area into a plurality of communicating cellular cavities of variable volumes.

The intermediate area may optionally be fed with a gas other than the one fed into the second portion.

In a preferred embodiment of the device according to the invention, supporting means are configured so as to support a multiplicity of independent membranes, which may be gathered together in two, three, four or even more independent groups. Thus, according to the type of programming for the control means and according to the number of membrane groups, it is possible to generate a large number of fluid flow modes in the first portion, for example, an essentially "horizontal" flow, an essen-tially "vertical" flow, a combination of vertical and horizontal flows, or even a "zig-zag" flow.

The number of flow modes may further be increased by providing the first portion of the culture chamber on the opposite side of the second portion, with a deformable pocket or one or more auxiliary deformable membranes supplied with gas, preferably with the selected gas by the pressurization circuit. However, it may be a different complementary gas, (in this case, it is clear that the pressurization circuit should include two parallel branches supplied with two different gases).

If several auxiliary membranes are used, they may be subdivided into independent groups (two, three, four or more), as previously explained for the other membranes. Each group may also be subdivided into independent subgroups, subject to adaptation of the gas supply mode for the groups (addition of supply ducts and valves).

Moreover, and always in this case, partitioning means may be provided in the central part of the first portion, defining within the latter, culture cavities each extending from a group of membranes to a group of auxiliary membranes, wherein each cavity is supplied with culture fluid. These partitioning means may include for example partitions made of a porous material to the culture fluid, but impervious to cells and tissues, so that only the culture fluid flows from one cavity to another.

On the other hand, the first portion may accommodate at least a deformable side membrane forming an interface between a side portion and the portion containing the cells or tissues, wherein the side portion is supplied with gas by the pressurization circuit and may discharge at least a portion of this gas. Of course, in this case, the control means are configured so as to determine, according to selected criteria, the pressure and the time for feeding in the gas, and for controlling access to the inlet and outlet of the side portion in order to control the shape of the side membrane (s). The gas introduced into this side portion may either be the gas selected for feeding the second portion, or another selected gas (with an additional branch in the pressurization circuit).

Preferably, each membrane, side membrane, auxiliary membrane and pocket is made of a porous material, at least in the direction pointing to the first portion which contains the cells or tissues to be grown, so that the selected gas may at least partially penetrate the first portion.

The device may comprise several culture chambers, for instance two or three, or even more. These chambers may be accommodated in a compartment and/or be external, whereby their connection to the pressurization circuit is achieved preferably via an interface.

The device according to the invention may include additional characteristics considered separately or combined and notably:

- the chamber is preferably delimited by a case comprising a lower portion forming a receptacle and an upper portion forming a lid, preferably transparent, wherein the supporting means comprises a frame accommodated within the receptacle and wherein appropriate cavities are defined, each for sealably supporting a membrane, to be supplied with selected gas and to accommodate this membrane when the pressure of the selected gas is lower than a threshold, and the frame is preferably made out of a synthetic material, particularly an elastomer;
- each inlet and each outlet is advantageously controlled by access control means driven by control means;
- each culture chamber may be connected to a first tank containing the culture fluid and a second tank for collecting the waste culture fluid, and form an autonomous culture unit; each tank preferably comprising at least a port provided with sealing means, particularly with a septum type, allowing fluid or any other body to be introduced therein or extracted therefrom;
- the compartment accommodating the control means and the pressurization circuit preferably comprises a sub-compartment forming a gas tank supplied with selected gas by the supplied inlet(s) and feeding the compressor; wherein the pressurization circuit then preferably includes a duct connecting an outlet of the sub-compartment to the inlet of the pocket or of the rear portion of the first portion, delimited by the auxiliary membrane(s);
- the sub-compartment may be subdivided into at least first and second sealed sub-portions forming a first low pressure gas tank, supplied with selected gas by each supply inlet and feeding the compressor, and a second high pressure gas tank fed by the compressor and supplying each outlet of the pressurization circuit with selected gas, respectively. A third sub-portion may also be provided between the first and second sub-portions so as to form a third intermediate pressure gas tank, wherein the different sub-portions communicate which each other through ports, access to which is controlled by control means, and each sub-portion may be supplied with selected gas, under the control of access control means driven by control means, each outlet of the pressurization circuit.

The invention also relates to a method for growing cells and tissues. This method notably consists of:

- a first step in which a culture device is provided, comprising at least a culture chamber provided with at least a deformable membrane at the interface between first and second portions with variable complementary volumes, wherein the first portion is able to be fed with a culture fluid and to receive cells and/or tissues to be grown, and the second portion is able to be supplied with gas; and
- a second step wherein the first and second portions are fed according to pressures, flow rates and times selected depending on criteria relating to the type of culture to be achieved, in order to change the shape of the membrane(s) during the culture period, so as to create a controlled flow of the culture fluid in the first portion of the chamber.

Preferably, in the first step, a chamber is provided, comprising a multiplicity of independent membranes, wherein more preferably these are gathered together in two, three or four groups of independent membranes, or even more, and in the second step, each group is independently supplied with selected gas so as to independently change the relevant shapes of the membranes of each group.

Also preferably, in the first step, it is expected that the first portion of the culture chamber comprises, on the opposite side to the second portion, a deformable pocket or one or more auxiliary membranes supplied with gas, preferably with the selected gas, and in the second step, the pocket or the membrane(s) are fed according to selected pressure, flow rates and times depending on the criteria, so as to change the shape of this pocket together with that of each membrane during the culture period. Advantageously, each membrane and the pocket or the auxiliary membrane are made of a porous material, at least in the direction pointing to the first portion, so that the selected gas, introduced in the second portion and/or the pocket or the auxiliary membrane, may at least partially penetrate the first portion.

Thus, as shown for the device, according to applied pressures, times and flow rates and according to the number of membrane groups used, it is possible to generate a large number of fluid flows in the first portion.

Other features and advantages of the invention will become apparent on examining the detailed specifications hereafter and the appended drawings, wherein:

FIG. 1 schematically illustrates a first embodiment of a culture device according to the invention, FIG. 2 illustrates in detail the culture chamber of the device in FIG. 1, FIGS. 3A–3C schematically illustrate, in sectional views, three different states of the lower membrane contained in the chamber of FIG. 2, which enable the culture fluid to flow, FIGS. 4A and 4B schematically illustrate, in sectional views, two different states of the lower membrane contained in the chamber of FIG. 2, which enable the waste culture fluid to be discharged, FIGS. 5A and 5B schematically illustrate, in sectional views, an alternative to the device of FIG. 2, in two different states of the supramembrane, placed above the lower membrane, FIG. 6 illustrates in detail an alternative culture chamber, with two lower and upper membranes, FIGS. 7A–7C schematically illustrates in sectional views, three different states of the lower and upper membranes contained in the chamber of FIG. 6, which enable the culture fluid to flow, FIGS. 8A and 8B schematically illustrate, in sectional views, two different states of the lower and upper membranes contained in the chamber of FIG. 6, which enable the waste culture fluid to be discharged, FIG. 9 illustrates, in an exploded view, another alternative to the culture chamber of the device of FIG. 1, with multiple lower membranes and deformable upper pocket, FIGS. 10A and 10B schematically illustrate, in sectional views, two different states of the lower membranes and of the upper pocket contained in the chamber of FIG. 9, which enable the culture fluid to flow, FIGS. 11A and 11B schematically illustrate, in top, unfolded, and side views, a culture unit including a chamber of the type illustrated in FIGS. 9 and 10, FIG. 12 illustrates an alternative to the device of FIG. 1, with two culture units, FIGS. 13A and 13B illustrate another alternative device according to the invention, with triple gas tank, FIGS. 14A–14C schematically illustrate three different states of the multiple lower membranes of the culture chamber of FIG. 9, FIGS. 15A and 15B schematically illustrate two different states of the multiple lower membranes and of the upper pocket of the culture chamber of FIG. 9, in a monophase type culture, FIGS. 16A and 16B schematically illustrate two different states of the multiple lower membranes and of the upper pocket of the culture chamber of FIG. 9, in a biphase type culture, FIGS. 17A and 17B schematically illustrate, in top and sectional views, two successive states of the multiple lower membranes and of the upper pocket of the culture chamber of FIG. 9, in a first example of a culture fluid flow mode, FIGS. 18A and 18B schematically illustrate, in top and sectional views, two successive states of the multiple lower membranes and of the upper pocket of the culture chamber of FIG. 9, in a second example of a culture fluid flow mode, FIGS. 19A–19D schematically illustrate, in top and sectional views, four successive states of the multiple lower membranes and of the upper pocket of the culture chamber of FIG. 9, in a third example of a culture fluid flow mode, FIGS. 20A and 20B schematically illustrate, in top and sectional views, two successive states of the multiple lower membranes and of the upper pocket of the culture chamber of FIG. 9, in a fourth example of a culture fluid flow mode, FIGS. 21A–21D schematically illustrate, in top and sectional views, four successive states of the multiple lower membranes and of the upper pocket of the culture chamber of FIG. 9, in a fifth example of a culture fluid flow mode, FIGS. 22A and 22B schematically illustrate, in top and sectional views, two successive states of the multiple lower membranes and of the upper pocket of the culture chamber of FIG. 9, in an example for the discharge mode of the waste culture fluid, and FIGS. 23A and 23B schematically illustrate, in top and sectional views, two successive states of the multiple lower membranes and of the upper pocket of the culture chamber of FIG. 9, in an example for the culture fluid feeding mode.

The appended drawings have essentially a definite character. Accordingly, they may not only serve to complete the invention, but also to contribute to its definition, if need be.

Reference is initially made to FIG. 1 in order to describe a first cell and tissue culture device, in a non-limiting embodiment.

The device illustrated in FIG. 1 includes a first compartment which accommodates a pressurization circuit 2, which will be described later on and control means 3, 4, for driving the device and which will also be described later on.

Said device also includes a second compartment 5 which accommodates a culture unit 6 including a culture chamber 7 connected to a first tank 8 for supplying culture fluid, as well as to a second tank 9 for collecting waste culture fluid. The pressurization circuit 2 is connected to the culture unit 6, so as to control its supply with culture fluid, as well as the flow of said culture fluid inside chamber 7, as described latter on.

As better illustrated in FIG. 2, the culture chamber 6 may be made as a case 10 including a portion, which will be termed as "lower", forming a receptacle 11, and another portion which will be termed "upper", forming a lid 12 appropriate for sealing the upper open part of the receptacle 11.

Preferably, lid 12 is removable so that cells and tissues to be grown may be introduced therein as well as optionally one or more culture supports.

Further, this lid is preferably transparent so that development of the culture may be observed.

Receptacle 11 (lower part of case 10) accommodates supporting means 13 for supporting, at a selected altitude with respect to the bottom of the receptacle 11, the peripheral rim of a membrane 14.

According to the invention, this membrane is made of a deformable material such as silicone, or polydimethylsiloxane (PDSM), or even polytetrafluorethylene (PTFE), or even dimethyl- and methylvinyl-siloxane polymers.

Membrane 14 forms in the culture chamber, an interface between a first upper portion 17 (upper portion 17 hereafter) and a second lower portion 16 (lower portion 16 hereafter) with variable complementary volumes.

Deformation of membrane 14 is produced by controlling pressures, flow rates and feed times, by the pressurization circuit 2, and under control of control means 3 and 4. To do this, receptacle 11 includes, in the upper portion 17, a first inlet 18 connected to a main branch 99 of pressurization circuit 2. Preferably, the first inlet 18 is in fact an inlet/outlet for feeding in a gas, under a selected pressure, inside the lower portion 16, as well as for extracting at least a portion of this gas.

Thus, as illustrated in FIGS. 3A–3C, according to the pressure of the gas which is fed in, via the inlet/outlet 18, inside the lower portion 16, the membrane is either accommodated inside the lower portion 16 (FIG. 3A), or inside the upper portion 17 (FIG. 3C), or at an intermediate level between the two aforementioned cases (FIG. 3B).

In actual fact, extracting the gas out of the lower portion 16 generates a depression which forces the membrane 14 to move nearer to the bottom of the receptacle 11 (FIG. 3A). On the other hand, feeding in a gas under a selected pressure (high pressure) inside this lower portion 16, via inlet 18, pushes the membrane 14 towards the upper portion 17 of the receptacle 11 (as illustrated in FIGS. 3B and 3C).

Advantageously, the receptacle 11 includes, in the upper portion 17, above the membrane 14, a second inlet 19 connected to the supply tank 8, as well as an outlet 20 connected to the collecting tank 9. Access to the different inlets and outlets 18, 19 and 20 is controlled by control means 3 and 4, preferably through solenoid valves.

These control means, once programmed, supply the cells or tissues which are first fed into the upper portion 17 of the chamber 6, above the membrane 14, with a stream of culture fluid, the pressure, flow rate and feed time parameters of which are, at each instant of the culture process, adapted to the needs of the latter. Flow of the culture fluid inside the upper portion 17 is controlled by the displacement of membrane 14, due to variations in pressure, flow rate and feed time of the gas in the lower portion 16.

In FIGS. 3A–3C, the level of the culture fluid inside chamber 6 is materialized by a horizontal line 21. As the gas pressure increases inside the lower portion 16, level 21 rises inside the upper portion 17, towards the lid 12.

Because of gas generation inside the upper portion 17, it is preferable to provide within the latter an inlet/outlet 22 for extracting the residual gas. Preferably, this inlet/outlet 22 has its access controlled by control means 3 and 4, but they may also be access control means manually operated by an operator. Furthermore, as illustrated in FIG. 2, this inlet/outlet 22 may also be directly formed in lid 12.

An example for supplying chamber 6 with culture fluid is illustrated in FIG. 4A. Advantageously, the culture fluid is introduced through inlet 19 into the upper portion 17 of receptacle 11, while a depression is formed inside the lower portion 16 of this same receptacle 11, through extracting the gas via the inlet/outlet 18.

An example for discharging the waste culture fluid is illustrated in FIG. 4B. In this discharge mode, the valve which controls access to the outlet 20 is open, while a high pressure gas is fed into the lower portion 16.

As better illustrated in FIG. 1, the culture chamber may include a third inlet 23, connected to an auxiliary branch 24 of the pressurization circuit 2. This auxiliary branch 24 opens into a gas tank 25 accommodated in the first compartment 1 of the device. This gas tank 25 is supplied with the selected gas through 1 or 2 gas supply lines 26 and 27, access to which is controlled by solenoid valves 28 and 29 driven by control means 3 and 4, respectively. Each supply line 26 and 27 is connected to an external gas tank, containing for example carbon dioxide or oxygen, or even air. Preferably, the gases which are fed into the gas tank 25, via lines 26 and 27 and which are intended to be fed into the lower portion 16, are selected in order to promote growth of cells and tissues inside the chamber 6. In other words, these gases have a double function: provide pressurization inside the lower portion 16 and participate in growing the cells and tissues inside the upper portion 17, in the same way as the culture fluid. To do this, advantageously, the deformable membrane 14 is porous, at least in the direction from the lower portion 16 towards the upper portion 17. Furthermore, this porosity is selected together with the high gas pressure, in order to effectively control the inflow rate of the gas inside the upper portion 17. Of course, in an alternative embodiment, membrane 14 may not be porous. In this case, chamber 6 should include, in its upper portion 17 an additional inlet for feeding in culture gas.

The main branch 99 of the pressurization circuit 2 is, as illustrated on FIG. 1, connected on the one hand, to a compressor 30 and, on the other hand to a gas tank 25. This compressor 30 is supplied with low pressure gas by the gas tank 25. Generally, in the Figures, the portions of the pressurization circuit which are supplied with low pressure gas are materialized by dashed lines, whereas portions of this circuit supplied with high pressure gas are materialized by continuous lines.

Of course, the compressor 30 is driven by control means 4.

Thanks to the main 99 and secondary 24 branches of the pressurization circuit 2, as well as to compressor 30, which feeds said main branch 99, it is possible to supply the lower portion 16 of chamber 6 with different gas pressures, according to needs.

The device may also include a discharge line 31 for discharging all or part of the gas contained inside the gas tank 25. This discharge line 31 is advantageously provided with access control by a valve 32 driven by control means 4. Thus all or part of the contents of gas tank 25, may be purged if required.

Furthermore, it is particularly advantageous when the device according to the invention comprises heating means 33 for heating the gas contained inside the gas tank 25. The temperature inside the chamber 6 may actually be regulated by thermal exchange between the gas and the culture fluid. This heating means 33 is provided for example as a heating resistor accommodated inside the gas tank 25 and controlled by control means 3. Temperature regulation is preferably performed in this case through temperature measurements supplied to control means 3 and 4 by a temperature sensor also accommodated inside tank 25. But, this sensor may be accommodated in chamber 6.

A gas analyzer 35 may also be provided inside the gas tank 25 for supplying control means 3 with representative measurements of the proportion (or percentage) of certain molecules within the gas tank 25. This analyzer may also serve for determining gas consumption in the chamber. In this way, control means 3 and 4 may precisely control the composition of the gas which is fed into the lower portion 16 of chamber 6 and which, when the membrane is porous, is intended to be mixed with the culture fluid inside the upper portion 17.

As shown in FIG. 13B, another temperature sensor 36 and/or a pH sensor may also be provided inside upper portion 17 of chamber 6. Other sensors may also be considered.

In short, the device may operate, either in a simple pre-programmed mode, or in a pre-programmed mode with self-regulation, according to whether it includes sensors which enable it to control the temperature of lower 16 and upper 17 portions of chamber 6 and/or the gas compositions of both these portions.

In the pre-programmed mode, the control means 4, before starting a culture process, are supplied with data for providing control over the culture. These data are stored in a rewritable memory. Alternatively, when the device is only intended for producing a single type of culture, the control means may only include a non-rewritable memory, or either hardware circuits directly. In the case of programming, as illustrated in FIG. 1, the device advantageously includes an interface 38, for example of the RS232 type connected to control means 3 and 4.

Such programming may be performed, for example, by introducing a series of n-tuples which defines the succession of operations which must be performed by the control means in order to ensure, in adequate conditions, growth of the cells and/or the tissues inside the culture chamber 6.

Each n-tuple may include, for example, at least a type of selected gas, a pressure for this selected gas, a feed rate for this selected gas, a culture fluid flow rate and a feed rate for this culture-fluid.

The sequence of operations associated with each one of these n-tuples, as defined by the programmed series, insures growth of the cells and/or tissues.

In the pre-programmed self-regulation operating mode, the control means are capable, on the basis of measurements which are supplied to them by different sensors, of modifying the n-tuple's parameters during the processing, so as to optimize the culture conditions inside the chamber. This may consist, for example in modifying the gas fed into the first lower portion 16, or in changing the temperature of this gas, or both at the same time, or even in increasing or reducing the relevant feed times for the gas and culture fluid.

The control means may comprise a microprocessor 4 with RAM and/or ROM memory, according to needs, coupled to a digital card 3 ensuring processing of the signals issued from sensors and analyzers.

Now, reference is made to FIGS. 5A and 5B in order to describe an alternative culture chamber for a device according to the invention.

What makes this culture chamber different from the one illustrated in FIG. 2, is the fact that it contains above the lower membrane 14, i.e. on the opposite side to the second lower portion 16, a deformable supramembrane 90 delimiting an intermediate area 91 with this lower membrane 14. In fact, in the illustrated example, the supramembrane 90 is firmly secured to the lower membrane 14 in a multiplicity of locations, in order to subdivide the intermediate area 91 into a plurality of alveolar cavities 92 communicating with each other and with variable volumes.

Chamber 6 comprises, at the upper portion 17, at least an inlet 93 connected to an outlet of pressurization circuit 2, access to which is controlled by a valve driven by the controller module 3, 4, in order to supply the intermediate area 91 with gas according to a selected pressure, a selected flow rate and selected times, depending on selected criteria, as well as at least an outlet 94 for discharging at least part of the gas from this intermediate area 91. This outlet 94 is also provided with access control by a valve driven by the controller module 3, 4 and preferably it communicates with the pressurization circuit 2.

The shapes of membrane 14 and supramembrane 90 and culture fluid flow may thereby be controlled together in the first portion 17.

The gas which is supplied to the intermediate area may be the selected gas which is supplied to the lower portion 16, or another gas. In the latter case, the pressurization circuit should be adapted so as to provide a double parallel supply with two different gases.

By submitting the supramembrane 90 to alternating high and low pressure cycles, a beating (or pulsating) mode may be established, especially useful when a tissue culture of the heart tissue type must be replicated.

In this alternative embodiment, deformation of membrane 14 provides macro-movements, whereas deformation of supramembrane 90 provides micro-movements.

Now, reference is made to FIGS. 6–8 for describing an alternate culture chamber for a device according to the invention.

What makes this culture chamber different from the one illustrated in FIG. 2, is the fact that it contains in the upper portion 17, another membrane 39 (upper) for controlling, together with membrane 14 (lower), fluid flow within the chamber 6.

This upper membrane 39 is, like lower membrane 14, supported by its rims at a level selected with respect to the lid 12. Thus, a gas may be fed in, with a selected flow rate, feed time and pressure between this upper membrane 39 and the lid 12 so as to control the deformation of the upper membrane.

The upper membrane 39 forms an interface in the upper portion 17 of the chamber 6, between a central portion 40, in which cells and/or tissues are placed and into which the culture fluid is injected, and a rear portion 41 into which the gas controlling the shape of membrane 39, is injected through an inlet/outlet 42 preferably formed within the lid 12.

This upper membrane 39 may be supported by supporting means firmly secured to receptacle 11, in its upper portion, or directly secured to lid 12.

Preferably, the gas which is used for deforming the upper membrane 39 is identical with the one used for deforming the lower membrane 14. However, it may also be different, subject to necessary adaptations of the culture chamber and pressurization circuit (two parallel supply branches, each coupled to inlet and outlet valves). Also, this upper membrane 39 is preferably porous, at least in the direction running from the rear portion 41 to the central portion 40, so that gas introduced into the rear portion 41 may be supplied to the central portion 40 for the tissue and/or cell culture.

Generally, porosity of the membranes (or the pockets) is selected so as to only concern gases and not cells. Accordingly, it may be advantageous if the membranes used in the device are porous in both directions, whereby, notably gases given off by the culture process in the upper portion are discharged from the lower portion 16.

In the example illustrated in FIGS. 7A–7C, both upper 39 and lower 14 membranes are submitted to pressures which are essentially in opposite phase. In other words, when one of the membranes is depressed, the other one is overpressed. But this might be otherwise, according to culture requirements. In this case, fluid flow within the chamber 6 is essentially vertical.

In FIG. 8A, an example for supplying chamber 6 with culture fluid is illustrated. In this example, culture fluid is fed in through inlet 19 inside the central portion 40, whereas gas is extracted from the first lower portion 16 by opening the valve which controls access to it. At the same time, the valve which controls access to inlet/outlet 42 of the rear portion 41 is closed.

In FIG. 8B, an example for discharging waste culture fluid is illustrated. In this example, both upper 39 and lower 14 membranes are simultaneously submitted to high pressures, by opening the valves which control access to inlets 18 and 42, while the valve controlling access to outlet 20 is closed.

In this alternative, a supramembrane 91 may be provided on the lower membrane 14 (like in the example illustrated in FIG. 5), and/or on the upper membrane 39 (of course subject to the necessary arrangements for the chamber and pressurization circuit).

Now, reference is made to FIG. 9 in order to describe another alternate culture chamber for a culture device according to the invention.

In this embodiment, culture chamber 6 is also delimited by a receptacle 11 cooperative with a lid 12. Upper membrane 39 of the chamber of FIG. 6, is replaced here with a deformable pocket 43 which may be firmly secured, either to the upper portion 17 of receptacle 11, or directly to lid 12.

Furthermore, instead of accommodating a single deformable lower membrane 14, receptacle 11 accommodates multiple deformable lower membranes independently of one another.

To do this, supporting means for the lower membranes are provided as a frame 44 wherein multiple cavities 45 are defined. Each cavity 45 is able to sealably support the peripheral rim of a lower membrane 46, to be supplied with gas, on the side of the lower portion 16 and to accommodate a membrane when the gas pressure inside the lower portion 16 is less than a threshold, for example when the gas has low pressure (depression).

Such a frame is for example made of an elastomeric material wherein gas supply ducts are integrally formed (not shown) and connected to the pressurization circuit 2 and feed the cavities either individually or collectively (in this case, it is advantageous that cavities from a same group communicate with each other).

This multiplicity of lower membranes 46 is advantageously subdivided into two groups, or more, for example, three, even four, as illustrated in FIG. 11A.

Thus, all the lower membranes belonging to a same group may be submitted to substantially identical pressure conditions, whereby these conditions may be different from one group to another. In the example, the frame includes four main ducts 47-1 to 47-4 (see FIG. 11A) for feeding the four groups of lower membrane 46-1 to 46-4, respectively.

In this case, and as better illustrated in FIG. 13, the pressurization circuit 2 includes four gas supply outlets 48-1 to 48-4 (forming the exit of the main branch 99), each of these outlets 48-$i$ ($i$=1 to 4, for this example) have their access controlled by a solenoid valve 49-$i$ driven by control means 3 and 4.

Thus, each group of lower membranes 46-$i$ may be controlled, regardless of other groups, by suitable pre-programming. In other words, programming the necessary operations for a given culture, consists in storing in the control means, a series of n-tuples of the type described earlier, but including each of the parameters relevant to each group.

As illustrated in FIG. 9, the receptacle 11 of the culture chamber 6 preferably, includes a port 51 adapted for sealably inserting the temperature sensor 36, as well as a second port 52 adapted for sealably inserting the pH sensor 37, inside the central portion 40 defined in the upper portion 17 by pocket 43.

Of course, this receptacle 11 also includes ports for letting in the ends of ducts 47-$i$ for supplying and extracting gas.

On the other hand, in the embodiment illustrated in FIG. 9, supply with culture fluid is notably achieved at two different levels preferably. To do this, frame 44 is advantageously equipped with a duct 53 including a substantially vertical portion provided with two outlets 54 and 55 for delivering the culture fluid at the lower membranes and at the deformable pocket 43, respectively. This achieves better distribution of culture fluid inside the central portion 40.

Also, a duct 56, with two inlets 57 and 58 placed at different levels are provided advantageously, so as to allow discharge of the waste culture fluid, at the lower membranes 46-$i$ and at the deformable pocket 43 respectively. These two inlets 57 and 58 may feed two discharge ducts, instead of one, wherein each duct has its access controlled by a valve driven by control means or operable by hand. This enables the residual gases which concentrate above the culture fluid in the monophase mode to be discharged and gas and/or culture fluid to be selectively extracted in the biphase mode.

The upper deformable pocket 43 is preferably provided as a porous membrane, at least in the direction from the inside of the pocket (or rear portion 41) towards the central portion 40. It may be made of the same material as that of the lower membrane(s) and upper membrane(s). This pocket acts, in fact, as the upper membrane 39 described earlier with reference to FIG. 6, notably.

For this reason, it includes an inlet/outlet 59 equivalent to inlet/outlet 42 and intended for introducing the gas and extracting it upon an order from the control means.

Thus, by controlling the gas supplies for the upper deformable pocket 43 and/or the lower membranes 46-$i$, it is possible to control the fluid flow within the central portion 40 of the culture chamber 6.

Preferably, as illustrated in FIGS. 11A and 11B, the culture chamber 6 is part of an autonomous culture unit 7, together with supply tanks 8 and collecting tanks 9. In this case, chamber 6 is connected to each tank via a duct 60, 61, the length of which is adapted in order to allow both tanks to be piled up on both sides of culture chamber 6, as illustrated in FIG. 11B. This solution is particularly interesting to the extent that it provides compactness of the culture unit 7.

As illustrated in FIGS. 1 and 12, each culture unit 7 may be accommodated inside compartment 5 of the device according to the invention. Such a compartment 5 may optionally (as illustrated in FIG. 12) accommodate two, or even more, culture units 7.

Furthermore, and as better illustrated in FIG. 13A, the device according to the invention, and notably its compartment 1 may be adapted for connection to an external culture chamber, or to an external culture unit, or even to several of them. To do this, the pressurization circuit 2 includes a bypass portion 62 comprising four bypass branches connected to solenoid valves 49-1 to 49-4 respectively and which therefore may be supplied with gas, in the same way as for outlets 48-1 to 48-4 of the main branch 99 of the pressurization circuit 2. However, these bypass branches may have their own solenoid valves for access control.

Preferably, connection of a culture unit 7 to the pressurization circuit 2 is made via an interface 63. Thus, it is particularly easy to connect a new unit for a new culture.

On the other hand, instead of accommodating a complete culture unit inside the second compartment 5 of the device, only one or more culture chambers 6 may be accommodated, wherein these are then connected to external tanks.

Finally, tanks 8 and 9 preferably include several leak-proof ports adapted so as to enable the culture fluid to be introduced (or to be extracted) or any other product. Such ports are for example equipped with a septum 65. Further, to maintain atmospheric pressure within the tank, these may be equipped with ports provided with filters 66.

On the other hand, and although this is not shown in the Figures, the tanks may provided with several flexible pockets containing different culture fluids, preferably and substantially at atmospheric pressure. In this case, the pockets are either connected to a distributor driven by control means or by hand, or each connected to a supply duct which opens in the upper portion 17 of chamber 6 and access to which is controlled by control means or by hand.

Reference is now made more particularly to FIG. 13A for describing an alternative embodiment of the pressurization circuit of the device according to the invention.

In this alternative embodiment, gas tank 25 is subdivided into three sub-portions 67, 68 and 69, wherein a low pressure (substantially atmospheric pressure), an intermediate pressure and a high pressure prevail, respectively.

The first sub-portion 67 is connected to gas supply ducts 26 and 27. This second sub-portion also communicates with the third sub-portion 68 through a port for which access is controlled by a valve 70.

The second sub-portion 68 preferably accommodates the compressor 30 which is fed through a duct 71 which opens in the first sub-portion 67. The compressor 30 feeds the third sub-portion 69 through a duct 72. This second sub-portion also communicates with the third sub-portion 69 through a port for which access is controlled by a valve 73.

Both valves 70 and 73 thus enable selected pressures to be established within each of the three sub-portions 67–69, under control of control means 3 and 4.

The third sub-portion 69 is connected to the pressurization circuit, and notably, to its main branch 99 for supplying high pressure gas.

The portion of the pressurization circuit 2 which is used for discharging the gas which is inside the lower portion 16 of each culture chamber 6, opens into the first sub-portion 67, so that the pressurization circuit 2 is a circuit of the closed type.

At the second sub-portion 68, placed at an intermediate pressure, an outlet 74 may be provided which feeds a valve 75, the outlet 100 of which is connected to inlet 59 of the upper pocket 43 (or to the rear portion 41 when the pocket is replaced with an upper membrane 39). Preferably, this valve 75 is also supplied with low pressure and high pressure gas from the first 67 and third 69 sub-portions of gas tank 25, so that the pocket 59 (or the rear of the upper membrane 39) may directly be supplied with a gas at the selected pressure, without it flowing through the compressor 30.

When the device is suitable for self-regulation, it is particularly advantageous when the molecule analyzer 35 is accommodated inside the first sub-portion 67, and when the heating resistor 33 and the temperature sensor 34 are accommodated in the third sub-portion 69.

On the other hand, it is also advantageous when each of the three sub-portions 67–69 is equipped with a pressure sensor 76 for delivering its internal pressure measurements to control means 3 and 4, so that the latter may precisely control pressures prevailing in each of the sub-portions.

Now reference is made more particularly to FIGS. 14–21 for describing different flow modes for the culture fluid inside the culture chamber 6.

As discussed earlier, the device according to the invention is intended for growing tissues and/or cells 78 in the central portion 40 of the culture chamber 6, by using a controlled environment consisting of culture fluid mixed with one or more selected gases.

To obtain optimum growth of these tissues and/or cells, the culture fluid should be in motion relatively to the cells and/or tissues. As illustrated in FIGS. 14A–14C, by a simple alternating, vertical displacement of the lower deformable membranes 46, the cells inside the central portion 40 of the culture chamber 6 may be displaced vertically and sideways. The multiplicity of lower membranes 46, especially when the membranes are in both of their states of extreme deformation (FIGS. 14A and 14C), enables cells and tissues to close in on one another, either because they are in an unstable equilibrium position or because they are forced to gather within cavities 45 defined by the frame 44.

Cells 78 may thus be displaced, whatever their position in the culture bath, thus preventing their accumulation in a region of limited extent. A fast inflation and deflation movement of the lower membranes considerably increases the homogeneity of the cell distribution within the culture medium (culture fluid plus gas). On the other hand, a slow inflation and deflation movement may cause areas of different cell concentrations to be generated within the chamber.

The device according to the invention is most particularly suitable for growing cells in the three dimensions on a support 77, and notably growing of tissues. Such supports 77 whatever their nature, may be placed on the lower membranes 46-i directly so that displacement of these lower membranes generates an effective stir, capable of significantly reducing the shear forces. In this way, an environment is provided which is particularly suitable for growing cells with high cell density.

As illustrated in FIGS. 15 and 16, several culture supports 77 may be accommodated inside a culture chamber. Notably, when the multiplicity of lower membranes is subdivided into groups, a support 77 may be provided for each group.

Such culture supports 77 may exhibit different geometries and natures, according to requirements, for example they may be spheroids (sphere-shaped pre-tissues) or suspended micro-carrier supports. Placing the support 77, individually, inside a porous envelope placed in the central portion 40, may also be considered, whereby this envelope is porous for the culture medium, but not for the cells. Thus, directly injected cells inside the envelope may continue to live and multiply whilst being confined on the support. Such an embodiment enables several types of cells or tissues to be grown inside a same chamber 6, without any risks of cross-contamination.

Of course, it is also possible to grow inside a same culture chamber 6, simultaneously, cells and/or tissues confined to the inside of envelopes, and cells and/or tissues non confined. Environments of the in vivo type may be simulated with such a variety of cultures.

As illustrated in FIGS. 15 and 16, the device according to the invention may provide monophase type (FIG. 15A and 15B) or biphase (FIGS. 16A and 16B) cultures. In the case of a monophase culture, nearly the whole of the central portion 40 of the culture chamber 6 contains a culture fluid, in the liquid phase, so that the culture support 77 and the tissues and/cells to be grown, are immersed in a culture liquid, almost permanently. However, for certain culture types, it is essential that the tissues and/or cells are not permanently immersed in the culture liquid. In this case, a biphase mode operation, of the type illustrated in FIGS. 16A and 16B, is particularly suitable. This mode consists in introducing a selected limited amount of gas like air for instance, above the liquid phase (materialized by grey portions). By displacing the lower membranes, possibly coupled to deformations of the upper pocket 43, the cells which are fixed on a culture support 77 may alternately be exposed to the liquid phase and the gas phase. By varying the amount of air and the displacement frequency of the lower membranes 46 and/or of the upper pocket 43, the device may control exposure time of the cells and/or tissues to the gas phase.

In this operating mode, it is particularly interesting when the duct 56 for extracting the culture medium out of the culture chamber 6, includes two inlets 57 and 58 placed at different levels, one 57 substantially placed at the lower membranes 46, and the other 58 substantially placed near the pocket 43. Inlet 57 of the discharged duct 56 is thus for discharging the liquid phase, whereas the upper inlet 58 of the same duct is for discharging the gas phase.

Now reference is made more particularly to FIGS. 17–21 for describing non-limiting flow mode examples for the culture fluid inside the central portion 40 of the culture chamber 6.

In the example illustrated in FIGS. 17A and 17B, the multiplicity of lower membranes is subdivided into two groups 46-1 and 46-2 placed on both sides of an axis XX in the culture chamber 6. The group of lower membranes, placed on the right of this axis XX is referenced here as 46-1 whereas the group of lower membranes placed on the left is referenced as 46-2. By having the right lower membranes 46-1 and the left lower membranes 46-2 move with opposite phase, the culture medium is forced to move alternately from left to right then from right to left. This provides an essentially horizontal flow.

In the example illustrated in FIGS. 18A and 18B, the multiplicity of lower membranes is also subdivided into two groups 46-1 and 46-2 placed on both sides of an axis YY perpendicular to axis XX of FIGS. 17, respectively. The lower membranes 46-1 are placed on the right of the transverse axis YY, whereas the lower membranes 46-2 are placed on the left of this axis. By having the right membranes 46-1 and the left membranes 46-2 move with opposite phase, the culture fluid is forced to move alternately from right to left then from left to right, with respect to axis YY. This also provides an essentially horizontal flow.

In both flow modes illustrated in FIGS. 17 and 18, varying the inflation state of the deformable pocket 43 is not absolutely necessary. The latter may be maintained in an inflated state during the alternating sequence right/left. Furthermore, in both cases, each group may be subdivided into sub-groups so as to precisely control the culture volume in the central portion 40. Actually, if for example the pocket 43 and one of the groups of lower membranes 46-i are maintained in an inflated state, the culture volume in the chamber is reduced, which, because of the concentration of culture fluid in the deflated portion, results in a reduction of the cell concentration in this fluid. In this case, relative displacements of the culture fluid and the cells may be provided by controlling the relevant inflations and deflations of the sub-groups of the group which is not maintained in the inflated state.

The flow mode illustrated in FIGS. 19A–19D is a cycle in four steps, requiring that the multiplicity of lower membranes be subdivided into four groups 46-1 to 46-4. During each step, only one of the groups of membranes is in its inflated state (membrane submitted to high pressure gas), whereas the other three groups are in a deflated state (membrane submitted to low pressure gas (or depression)). Thus, the culture fluid, which is substan-tially placed in the region located above the group of lower membranes which pass from a deflated state to an inflated state, is forced to return to the regions located above the other three groups, the membranes of which pass from the inflated state to the deflated state or remain in the deflated state. This provides permanent displacement of the culture fluid, in the horizontal plane, in all directions.

The flow mode illustrated in FIGS. 20A and 20B is a cycle in two steps, in which the multiplicity of lower membranes is also subdivided into four groups 46-i. In this mode, both groups of lower membranes 46-1 and 46-3 substantially placed on a diagonal, move with opposite phase with respect to both other groups 46-2 and 46-4 substantially placed according to the other diagonal.

Thus, the state of each group of lower membranes alternates from the inflated state to the deflated state, and the culture medium, which is in the region substantially placed above the lower membranes which have their state passing from the deflated state to the inflated state, is forced to return to both regions which are substantially placed above the membranes, which have their state changing from the inflated state to the deflated state.

The culture medium is therefore forced to move in two directions essentially perpendicular to each other, from left to right and from back to front. In the flow modes illustrated in FIGS. 19 and 20, it is also preferable that the deformable upper pocket 43 remains in its inflated state throughout the cycles or in a "free" state wherein it is substantially at atmospheric pressure (being directly fed by the first subportion 67 of gas tank 25). This last case provides self-regulation of the pressure in chamber 6, because the pocket's volume may automatically be adapted to pressure variations in said chamber.

The flow mode illustrated in FIGS. 21A–21D is a cycle in four steps, ensuring a circular movement, in the horizontal plane, of the culture medium. This flow mode also requires that the multiplicity of lower membranes be subdivided into four groups 46-1 to 46-4. Here, in each step, only one of the groups of membranes is placed in a deflated state, whereas the other three groups of membranes are placed in an inflated state. The culture fluid, which is in the region placed substantially above the group of lower membranes having their state passing from the deflated state to the inflated state, is therefore forced to return to the region which is substan-tially placed above the lower membranes having their state passing from the inflated state to the deflated state.

Accordingly, the culture fluid which moves in a first direction, during a first step, is forced to move along a second direction perpendicular to the first direction during the second step and so forth. This mode is most particularly suitable for moving cells, spheroids and micro-carriers inside the central portion 40, subject to observance of decantation phases.

In this flow mode, it is preferable that the upper deformable pocket 43 be maintained in its free-state (as defined above) during the successive cycles.

Now, reference is made to FIGS. 22A and 22B for describing a discharge mode for the waste culture fluid.

In this example, two successive steps may be implemented. In the first step (FIG. 22A) the valves controlling the inlet of fluid supply duct 53 and the outlet of the fluid discharged duct 56 are closed. All the lower membranes 46-i are placed in the deflated state, whereas the valve controlling access to the upper deformable pocket 43 is open. Pocket 43 is therefore forced to fully inflate. In the second step (FIG. 22B), the valve controlling the inlet of supply duct 53 is maintained closed, whereas the one controlling the outlet of discharged duct 56 is open. At the same time, the valve controlling access to the upper deformable pocket 43 is closed while the lower membranes 46 are placed in their inflated state. As a result, culture fluid is forced to discharge from culture chamber 6 through duct 56.

Now, reference is made to FIGS. 23A and 23B in order to describe a mode for supplying the culture chamber with culture fluid. This mode also includes two steps. In a first step (FIG. 23A), the access valves at the inlet of supply duct 53 and at the inlet of discharged duct 56 are maintained in a closed position, whereas the access valve at the inlet/outlet 59 of the deformable upper pocket 43 is placed in an open position. At the same time, both groups 46-2 and 46-3 of lower membranes, placed to the left of transverse axis YY, are placed, in the deflated state, while both groups 46-1 and 46-4, placed to the right of this same axis, are placed in the inflated state. The upper pocket 43 gradually deflates while the culture fluid is concentrated in the region substantially located above the deflated groups of lower membranes 46-2 and 46-3.

In the second step, the access control valve at the outlet of the discharged duct 56 is maintained in the closed state, whereas the access control valve at the inlet of supply duct 53 is placed in the open state. At the same time, the valve controlling the inlet/outlet 59 of the deformable upper pocket 43 is closed and the whole of lower membranes 46-i are placed in the deflated state, thus enabling the culture fluid to penetrate inside the central portion 40 of the culture chamber 6.

Such a supply mode provides maximum substitution of the culture medium. The volume of exchanged fluid may be controlled by reducing the number of lower membrane groups involved in the supply cycle.

In the above, devices were described in which access to inlets or outlets of the culture chamber was controlled by valves, and more particularly by solenoid valves driven by control means 3 and 4. However, any other type of access control means may be considered, and notably means including a flexible duct with thinned walls accommodated in a case connected to a pressurization circuit so that either a high pressure gas forcing contact of the thinned walls of the duct or a low pressure gas for moving apart these thinned walls away from each other, may be fed into said case and therefore letting the gas or the fluid pass inside the duct.

Furthermore, the device may include a multiplicity of lower membranes and a multiplicity of upper membranes.

For example, each multiplicity may be subdivided into groups and/or into sub-groups, wherein the number of groups and/or sub-groups of lower membranes is not necessarily identical to that of upper membranes. In the case of an identical number, provision in the central portion 40 of partitioning means defining within the latter culture cavities extending each from a group of lower membranes 46-$i$ to a group of upper membranes, may be advantageous. Each cavity is configured in this case so as to be supplied with culture fluid and/or gas. For this purpose, it is advantageous if the partitioning means include partitions made of a porous material to the culture fluid and to the gas, but impervious to cells and tissues. The culture chamber may thus be subdivided into a multiplicity of culture sub-chambers able to grow cells and/or tissues whether different or not, in parallel.

Further, the first upper portion 17 may accommodate at least a deformable side membrane defining an interface between a side portion and the central portion 40 containing the cells or tissues. In this case, the side portion includes an inlet supplied with gas by an outlet of the pressurization circuit 2 and an outlet for discharging at least a portion of this gas out of the chamber, and preferably into the pressurization circuit. The control means 3, 4 are then configured for determining, according to selected criteria, the pressure and gas feed time, and for controlling access to the inlet and outlet of the side portion so as to control the shape of the side membrane. The number of flow modes in the chamber may thus be increased.

The gas fed into the side portion may be the selected gas which feeds the lower portion 16, but it may also be another gas, subject to necessary adaptation of the culture chamber and of the pressurization circuit (two parallel supply branches each coupled to inlet and outlet valves).

On the other hand, in the above, reference is made to a pressurization circuit of the closed type. But the invention is also related to "open" pressurization circuits which include, for example one (or more) gas tank(s) connected via one (or more) valve(s) to the inlet (or to the inlets) of the lower portion 16 and/or of the side portion and/or the rear portion 41 of the culture chamber. In this case, the outlet(s) of the relevant portion(s) may directly communicate with the outside world, whereby the gas or the gases ensuring pressurization of the membranes and/or the pocket are then not reused in the pressurization circuit.

In short, the device according to the invention acts as a pump which provides several combined functions and notably a molecular exchange at gas level, a stirring/flow of culture fluid and of cells and/or tissues and a thermal exchange between gas and culture fluid.

The invention is not limited to the sole devices for growing cells and tissues which have just been described, as non-limiting examples. The invention also relates to a method for growing cells and tissues which includes two steps.

The first step consists in providing a culture device of the type described above, and comprising at least a culture chamber, provided with at least a deformable membrane placed at the interface between the first and second portions with variable complementary volumes, wherein the first portion (upper) may be supplied with culture fluid and receives cells and tissues to be grown, and the second portion (lower) is supplied with a gas.

The second step consists in feeding the first and second portions according to pressure, flow rates and times selected depending on criteria relating to the type of culture to be achieved, so as to vary the shape of the membrane(s) throughout the culture period, thereby generating a controlled flow of the culture fluid inside the portion of the chamber.

Preferably, in the first step of this method, the chamber does not comprise a single membrane, but a multiplicity of independent membranes, wherein the latter are more preferably subdivided into at least two independent groups.

In this case, it is particularly advantageous if during the second step, each group is supplied with the selected gas, regardless of the other groups so that the relevant shapes of membranes of each group vary independently.

In the first step of the method according to the invention, a deformable pocket supplied with gas may also be provided, inside the first portion of the culture chamber, on the opposite side to the second portion. In this case, during the second step, the pocket is fed according to pressures, flow rates and times selected in accordance with the aforementioned culture criteria, so as to vary the shape of the pocket together with that of each membrane, during the culture period.

As an alternative, the upper deformable pocket may be replaced with one or more deformable auxiliary membranes placed at the interface between a central portion receiving the cells or tissues to be grown and a rear portion supplied with gas. Further, it is advantageous when during the first step, the second portion and the pocket or the rear portion are supplied with the same selected gas.

It is also advantageous if each membrane and the pocket or the auxiliary membrane are made of porous material, at least in the direction pointing towards the first portion (central portion), so that the selected gas for varying the shapes of the membranes and of the pocket may at least partially penetrate the first portion (central portion) so as to participate in the culture process with the culture fluid.

All the flow modes which have been described in the part concerning the devices according to the invention, may also be considered as examples for the second step of the method according to the invention. Notably, a displacement of the fluid and/or the cells and tissues is provided by the method, thanks to its second step, so as to generate in the culture chambers, areas in which cell concentrations are different from one another.

The invention applies to a great number of types of cells and tissues, such as notably:

intestinal cells: Intestine 407, Caco-2, Colo 205, T84, SW1116, WiDr, HT 115, HT 55;

endothelial cells: HAOSMC (Human Aortic Smooth Muscle Cells);

epidermal cells: NHEK-Neopooled (Human Epidermal Keratinocyte Neonatal), Equine Dermis;

cancer cells: Hela, CHO-K1;

fibroplastic cells of the intestinal type: CCD-18Co;

fibroplastic cells of type MRC-5, 3T3, Wi-38 myeloma: SP2O-Ag14, P3X63 Ag8 653, MPC11;

hybridoma;

insect cells: SF9.

Of course, certain of these tissues or certain of these cells require use of a culture support, as stated earlier.

This list is absolutely not exhaustive; these are only examples.

The device according to the invention may include additional features to the ones presented above, and notably:

the pressurization circuit may include at least an inlet connected to a tank which contains the selected gas and at least an outlet which feeds the inlet of the second portion;

- the pocket may comprise a membrane;
- the first portion may include at least an inlet able to be supplied with culture fluid by the first tank and at least an outlet able to discharge the waste culture fluid into a second tank, and the control means may be configured so as to control access to different inlets and outlets of the first and second portions so as to control together the shape of the membrane, the culture fluid supply and the flow of this fluid in the first portion. In this case, it is advantageous when the pressurization circuit is of the closed type and includes at least an inlet able to supply it with selected gas, a compressor able to deliver the selected gas under the selected pressure, and at least an outlet fed by this compressor and able to feed the inlet of the second portion;
- the supporting means may be configured for supporting a multiplicity of independent membranes. In this case, the multiplicity may be subdivided in at least two groups of independent membranes, wherein the second portion then includes at least two inlets for supplying with the selected gas each group of membranes, and wherein the control means are configured for controlling access to both these inlets so as to control the relevant shapes of membranes of each group. As an alternative, the multiplicity may be subdivided into four groups of independent membranes, the second portion including four inlets for supplying with the selected gas each group of membranes, independently, and wherein the control means are configured for controlling access to these four inlets so as to control the relevant shapes of membranes of each group;
- the culture chamber may accommodate in the first portion, on the opposite side to the second portion, auxiliary supporting means able to support at least a deformable auxiliary membrane forming in this first portion an interface between a central portion able to receive cells or tissues to be grown and a rear portion including an inlet, and a rear portion including an inlet able to be supplied with gas by the pressurization circuit and an outlet connected to this pressurizing circuit, wherein the control means are configured for determining, according to criteria relating to the type of culture to be achieved, the pressure and the time for feeding this gas, and for controlling access to the inlet and to the outlet of the rear portion so as to control the shape of the auxiliary membrane together with the shape of each membrane;
- the pressurization circuit may include another inlet able to supply with selected gas, under another selected pressure, the inlet of the pocket or of the rear portion;
- the inlet and the outlet of the pocket or of the rear portion may be merged;
- the auxiliary supporting means may be configured for supporting a multiplicity of independent auxiliary membranes. In this case, it is advantageous if the multiplicity is subdivided into at least two groups of independent auxiliary membranes, wherein the rear portion includes at least two inlets for supplying with selected gas each group of auxiliary membranes, independently, and the control means are configured for controlling access to both these inlets so as to control the relevant shapes of the auxiliary membranes of each group;
- the inlet and the outlet of the second portion may be merged;
- the culture chamber may be delimited by a case comprising a lower portion forming a receptacle including a port for each inlet and for each outlet of the first and second portions of the chamber. This receptacle may include a port for each inlet and for each outlet of the second portion of the chamber, wherein the lid then includes an adapted port for the inlet and for the outlet of the pocket or of the rear portion, and auxiliary supporting means are firmly secured to the lid;
- at least a probe may be provided, selected from at least a pH probe, and a temperature probe, connected to control means and able to be inserted into the inside of the first portion of the chamber, wherein the receptacle then includes at least a first auxiliary port adapted for insertion of each probe;
- two inlets driven by control means and able to be supplied with a first and second selected gas may be provided, respectively;
- each inlet and each outlet may be controlled by an access control means driven by control means;
- the supporting means may include a frame accommodated in the receptacle and preferably made of a synthetic material, in particular an elastomer;
- the first portion may accommodate at least a deformable side membrane forming in the first portion an interface between a side portion and the portion containing cells or tissues, wherein the side portion comprises an inlet able to be supplied with gas by the pressurization circuit and an outlet for discharging at least a portion of this gas, and the control means are configured for determining, according to selected criteria, the pressure and time for introducing the gas, and for controlling access to the inlet and outlet of the side portion so as to control the shape of the side membrane. In this case, it is advan-tageous when the gas fed into the side portion is the selected gas;
- at least one of the first and second tanks may comprise at least a flexible pocket-tank able to supply with culture fluid the first portion or to collect the waste fluid. In this case, it is advantageous when at least the first tank comprises at least two flexible pocket-tanks able to supply the first portion with different culture fluids;
- the control means and the pressurization circuit (2) may be accommodated in a first compartment, whereas a second compartment accommodates the culture unit. In this case it is advantageous when the second compartment accommodates at least another culture unit, and when the pressurization circuit comprises at least a first bypass portion, connected to each of its outlets which deliver the gas under the selected pressure, so as to supply at least the other culture unit with gas;
- the pressurization circuit may comprise a second bypass portion, connected to each of its outlets delivering the gas under the selected pressure so as to supply at least an external culture unit with gas;
- the first compartment may comprise a sub-compartment forming a gas tank fed by each inlet supplying the selected gas and feeding the compressor, and which may accommodate a temperature sensor configured for delivering temperature measurements to the control means as well as gas heating means driven by control means according to selected criteria and temperature measurements. It is also advantageous when the sub-compartment accommodates a gas analyzer configured for delivering to the control means measurements representing the percentage of at least a species of molecules inside the sub-compartment, and when the control means are configured for controlling access to various inlets and outlets according to selected criteria and percentage measurements. Furthermore, the pressuri-zation circuit may include a duct connecting at least an outlet of the sub-compartment to the inlet of the pocket or of the rear portion of the first portion. On the other hand, the sub-compartment may be subdivided into at least first and second leak-proof sub-portions forming a first low pressure gas tank, fed by each inlet supplying selected gas and feeding the compressor, and a second high pressure gas tank fed by the compressor and supplying each outlet of the pressurization circuit with selected gas. In this case, it is advantageous when the first sub-portion of the sub-compartment accommodates the gas analyzer and the second sub-portion of the sub-compartment accommodates the temperature sensor and the gas heating means.

Also, the method according to the invention may include additional features to those presented above, and notably:

in the second step, differences in cell concentrations may be obtained by different initial cell concentrations in culture areas and/or deformation cycles of the membranes and/or the pocket which differ from one area to another;

the second step may be able to provide together control of the pressure and of the culture fluid flow in the first portion of the chamber;

in the first step, partitioning means defining culture cavities which extend each from a group of membranes to a group of auxiliary membranes, and each able to be supplied with culture fluid and to receive adhering cells as well as culture supports and/or non-adhering cells and/or tissues, possibly different from one cavity to another, may be provided in the first portion.

The invention is not limited to the embodiments of devices and methods described above, only as examples, but it encompasses all alternative embodiments which may be considered by one skilled in the art within the scope of the claims hereafter.

What is claimed is:

1. A cell and tissue culture device, wherein it comprises:
a pressurization circuit (2) configured so as to deliver at least one selected gas under a selected pressure,
at beast one culture chamber (6) accommodating a support (13) for supporting at least one deformable membrane (14; 46-i) forming within the chamber (6) an interface between first (17) and second (16) portions with variable complementary volumes, wherein said first portion (17) is configured for receiving cells and/or tissues to be grown and for being supplied with culture fluid from a first tank (8), and said second portion (16) comprising an inlet/outlet (18; 47-i) able to be supplied with gas from said pressurization circuit (2) and to discharge at least a portion of this gas, and
control equipment (3,4) configured for determining, according to selected criteria related to the type of culture to be achieved, the gas to be fed into the second portion (16), its pressure and feed time of this gas, and controlling access to first (17) and second (16) portions of the chamber (6) so as to control together the shape of the membrane (14; 46-i), the culture fluid supply and the flow of this fluid in the first portion (17).

2. A device according to claim 1, wherein it includes a supramembrane (90) placed above the membrane (14), on the side of the first portion (17) and delimiting with this membrane (14) at least one intermediate area (91), in that said chamber (6) comprises at least an inlet (93) able to be supplied with gas through the pressurization circuit (2) and to supply with said gas said intermediate area (91) and at least one outlet (94) for discharging from this intermediate area (91) at least a portion of the gas, and in that said control equipment (3, 4) is configured for determining, according to selected criteria, the gas to fed into the intermediate area (91), its pressure and the time for feeding in this gas, and for controlling access to inlet (93) and outlet (94) of this intermediate area (91) so as to control together the shapes of the membrane (14; 46-i) and supramembrane (90) and the flow of the culture fluid in the first portion (17).

3. A device according to claim 2, wherein the supramembrane (90) is firmly secured to membrane (14) in a multiplicity of selected locations, so as to subdivide the intermediate area (91) into a plurality of alveolar cavities (92) communicating with each other with variable volumes.

4. A device according to claim 1, wherein said pressurization circuit (2) includes at least one inlet connected to a tank containing said selected gas and at least one outlet (99) feeding the inlet (18; 47-i) of the second portion (16).

5. A device according to claim 1, wherein said first portion (17) comprises at least one inlet (19) able to be supplied with culture fluid by said first tank (8) and at least one outlet (20) able to discharge waste culture fluid into a second tank (9), and in that said control equipment (3,4) is configured in order to control access to the different inlets and outlets of first (17) and second (16) portions so as to control together the shape of the membrane (14; 46-i), the culture fluid supply and the flow of this fluid in the first portion (17).

6. A device according to claim 5, wherein that said pressurization circuit (2) is a closed circuit and includes at least one inlet (26,27) able to supply it with a selected gas, a compressor (30) able to deliver the selected gas under the selected pressure and at least one outlet (99) fed by said compressor (30) and able to feed inlet (18; 47-i) of the second portion (16).

7. A device according to claim 1, wherein said support (13) is configured for supporting a multiplicity of independent membranes.

8. A device according to claim 7, wherein said multiplicity is subdivided into at least two groups of independent membranes, in that said second portion (16) includes at least two inlets (47-i) for supplying with a selected gas each group of membranes (46-i), independently, and in that said control equipment (3,4) is configured for controlling access to both these inlets (48-i) so as to control the relevant shapes of the membranes of each group.

9. A device according to claim 7, wherein said multiplicity is subdivided into four groups of independent membranes, in that said second portion (16) includes four inlets (47-i) for supplying with gas each group of membranes, independently, and in that said control (3,4) is configured for controlling access to these four inlets so as to control the relevant shapes of the membranes of each group (46-i).

10. A device according to claim 1, wherein said culture chamber (6) is accommodated in the first portion (17), on the opposite side to the second portion (16), a deformable pocket (43) is provided with an inlet (59) supplied with gas by the pressurization circuit (2) and an outlet (59) connected to this pressurization circuit (2), and in that said control equipment (3,4) is configured for determining, according to said criteria related to the type of culture to be achieved, the pressure and the time for feeding this gas, and for controlling access to the inlet and to the outlet of the pocket (43) so as to control its shape together with shape of each (46-i).

11. A device according to claim 10, wherein said pocket (43) comprises a membrane.

12. A device according to claim 1, wherein said culture chamber (6) is accommodated in the first portion (17), on the opposite side to the second portion (16), an auxiliary support (12) able to support at least a deformable auxiliary membrane (39) which forms in the first portion (17) an interface between a central portion (40) able to receive cells or tissues to be grown and a rear portion (41) including an inlet (42) able to be supplied with gas by the pressurization circuit (2) and an outlet (42) connected to this pressurization circuit (2), and in that said control equipment (3,4) is configured for determining, according to said criteria related to the type of culture to be achieved, the pressure and the time for feeding this gas, and for controlling access to the inlet and to the outlet of the rear portion (41) so as to control the shape of the auxiliary membrane (39) together with the shape of each membrane (14; 46-i).

13. A device according to claim 10, wherein said pressurization circuit (2) includes another outlet (100) able to supply with said selected gas, under another selected pressure, the inlet (59; 42) of the pocket (43) or of the rear portion (41).

14. A device according to claim 10, wherein the inlet and the outlet of the pocket (43) or the rear portion (41) are merged.

15. A device according to claim 10, wherein said auxiliary support (12) is configured for supporting a multiplicity of auxiliary independent membranes.

16. A device according to claim 15, wherein said multiplicity is subdivided into at least two groups of independent auxiliary membranes, in that said rear part (41) includes at least two inlets for supplying with selected gas each group of auxiliary membranes, independently, and in that said control equipment (3,4) is configured for controlling access to both these inlets so as to control the relevant shapes of the auxiliary membranes of each group.

17. A device according to claim 15, wherein said multiplicity is subdivided into four groups of independent auxiliary membranes, in that said rear part (41) includes four inlets for supplying with selected gas each group of auxiliary membranes, independently, and in that said control equipment (3,4) is configured for controlling access to these four inlets so as to control the relevant shapes of the auxiliary membranes of each group.

18. A device according to claim 16, wherein the central portion (40) of the first portion (17) accommodates at least one partition defining in said central portion culture cavities each extending from a group of membranes (46-i) to a group of auxiliary membranes, wherein each cavity is able to be supplied with culture fluid.

19. A device according to claim 18, wherein said partition includes partitions made of a porous material to said culture fluid, but impervious to cells and tissues, so that said culture fluid may flow from one cavity to another.

20. A device according to claim 1, wherein the first portion (17) includes at least one port provided with a seal, enabling cells or tissues to be introduced therein or extracted therefrom.

21. A device according to claim 1, wherein the inlet and the outlet (18; 47-i) of the second portion (16) are merged.

22. A device according to claim 1, wherein membranes (14; 43; 46-i) and auxiliary membrane (39) are made of a porous material, at least in the direction pointing to the first portion (17), so that the selected gas, fed into the second portion (16), may at least partially penetrate said first portion (17).

23. A device according to claim 5, wherein said culture chamber (6) is delimited by a case comprising a lower portion forming a receptacle (11), including at least including at least the inlet (19) supplying the culture fluid, the outlet (20) for discharging the waste culture fluid, the inlet/outlet (19) for supplying the selected gas of the second portion (16) or for discharging at least a portion of this gas and the outlet (22) connected to the pressurization circuit (2), an upper portion forming a lid (12), and in that said support comprises a frame (44) accommodated in the receptacle (11) and wherein cavities (45-i) are defined each able to sealably support a membrane (46-i), to be supplied with said selected gas and to accommodate said membrane when the pressure of the selected gas is below a first threshold.

24. A device according to claim 23, wherein said lid (12) is made of a transparent material.

25. A device according to claim 23, wherein said lid (12) comprises an inlet/outlet (42; 59) of pocket (43), or of the rear portion (41), and in that said auxiliary support is firmly secured to said lid (12).

26. A device according to claim 23, wherein it comprises at least one probe, selected from at least a pH probe (37) and a temperature probe (36), connected to said control equipment (3) and able to be introduced inside the first portion (17 of chamber (6), and in that said receptacle (11) includes at least one adapted first auxiliary port (52,51) for introducing each probe (36,37).

27. A device according to claim 1, wherein it comprises two inlets (26,27) driven by said control equipment (3,4) and able to be supplied with the first and second selected gas, respectively.

28. A device according to claim 1, wherein each inlet and each outlet is controlled by an access control device (28; 29; 32; 49-i; 75) driven by said control equipment (3,4).

29. A device according to claim 23, wherein said frame (44) is made of an elastomer.

30. A device according to claim 1, wherein said first portion (17) accommodates at least one deformable side membrane forming in the first portion (17) an interface between a side portion and the portion containing (40) the cells or tissues, said side portion comprising an inlet able to be supplied with gas by said pressurization circuit (2) and an outlet for discharging at least a portion of this gas, and in that said control equipment (3,4) is configured for determining, according go selected criteria, the pressure and the time for introducing the gas, and for controlling access to the inlet and outlet of the side portion so as to control the shape of the side membrane.

31. A device according to claim 30, wherein said gas fed into said side portion is the selected gas.

32. A device according to claim 1, wherein it comprises at least one culture unit (7) including the first tank (8) connected to the culture chamber (6) and a second tank (9) connected to this culture chamber (6) so as to collect the waste culture fluid.

33. A device according to claim 32, wherein each first (8) and second (9) tank comprises at least one port provided with a leak-proof seal (65), enabling fluid to be introduced therein or extracted therefrom.

34. A device according to claim 1, wherein at least one of the first (8) and second (9) tanks comprises at least one flexible pocket-tank able to supply with culture fluid said first portion (17) or to collect the waste fluid.

35. A device according to claim 34, wherein at least the first tank (8) comprises at least two flexible pocket-tanks able to supply with different culture fluids said first portion (17).

36. A device according to claim 32, wherein it comprises a first compartment (1) accommodating said control equipment (3,4) and pressurization circuit (2), and a second compartment (5) accommodating said culture unit (7).

37. A device according to claim 36, wherein said second compartment (5) accommodates at least another culture unit, and in that said pressurization circuit (2) comprises at least a first bypass portion, connected to each of its outlets (99) delivering said gas under the selected pressure, so as to supply with gas at least the other culture unit.

38. A device according to claim 32, wherein said pressurization circuit (2) comprises a second bypass portion (62), connected to each of its outlets (99) delivering said gas under the selected pressure, so as to supply with gas at least an external culture unit.

39. A device according to claim 36, wherein said first compartment (1) comprises a sub-compartment (25) forming a gas tank supplied with selected gas by each supply inlet (26; 27) and feeding said compressor (30).

40. A device according to claim 39, wherein said sub-compartment (25) accommodates a temperature sensor (34) configured for delivering temperature measurements to the control equipment (3,4) and a gas heater (33) driven by said control equipment (3,4) according to said selected criteria and said temperature measurements.

41. A device according to claim 39, wherein said sub-compartment (25) accommodates a gas analyzer (35) configured for delivering to the control equipment (3,4) representative measurements of the percentage of at least one species of molecules inside said sub-compartment (25), and in that said control equipment (3,4) is configured for controlling access to the different inlets and outlets according to said selected criteria and said percentage measurements.

42. A device according to claim 39, wherein said pressurization circuit (2) includes a duct (100) connecting at least one outlet (74) of said sub-compartment (25) to the inlet (59; 42) of said pocket (43) or of said rear portion (41) of the first portion (17).

43. A device according to claim 39, wherein said sub-compartment (25) is subdivided into at least first (67) and second (69) leak-proof sub-portions forming a first low pressure gas tank, supplied with selected gas by each supply inlet (26; 27) and feeding said compressor (30), and a second high pressure gas tank fed by said compressor (30) and supplying each outlet (99,62) of the pressurization circuit (2) with selected gas.

44. A device according to claim 43, wherein the first sub-portion (67) of sub-compartment (25) accommodates said gas analyzer (35) and the second sub-portion (69) of sub-compartment (25) accommodates said temperature sensor (34) and said gas heater (33).

45. A device according to claim 43, wherein said sub-compartment (25) is subdivided Into first (67), second (69) and third (68) leak-proof sub-portions, wherein said third (68) sub-portion is placed between the first (67) and second (69) sub-portions and forming a third intermediate pressure gas tank, said sub-portions communicating with one another through a port with access control by said control equipment (3,4).

46. A device according to claim 43, wherein each sub-portion (67-69) supplies with selected gas, under control of an access control device (49-i) driven by said control equipment, each outlet (100,48-i) of the pressurization circuit, delivering said selected gas to said culture chamber.

47. A method for growing cells and tissues, wherein it comprises:
a first step wherein a culture device is provided, comprising at least a culture chamber provided with at least a deformable membrane at the interface between the first and second portions with variable complementary volumes, wherein said first portion is able to be supplied with a culture fluid and to receive cells and/or tissues to be grown, and said second portion is able to be supplied with a gas; and
a second step wherein said first and second portions are fed according to pressures, flow rates and selected times, depending on criteria relating to the type of culture to be achieved, in order to vary the shape of this membrane during the culture period so as to generate a controlled flow of the culture fluid in the first.portion of the chamber.

48. A method according to claim 47, wherein in the first step, a chamber is provided comprising a multiplicity of independent membranes.

49. A method according to claim 48, wherein in the first step, a subdivision of the multiplicity into at least two groups of independent membranes is provided, and in that in the second step each group is independently supplied with selected gas so as to vary the relevant shapes of the membranes of each group, independently.

50. A method according to claim 49, wherein in the first step, a subdivision of the multiplicity into at least four groups of independent membranes is provided, and in that in the second step each group is independently supplied with selected gas so as to vary the relevant shapes of the membranes of each group, independently.

51. A method according to claim 48, wherein the first step, a deformable pocket supplied with gas is provided in the first portion of the culture chamber, on the opposite side to the second part and in that in the second step said pocket is fed according to selected pressures, flow rates and times depending on said criteria, in order to vary the shape of this pocket together with that of each membrane during the culture period so as generate culture fluid flow.

52. A method according to claim 48, wherein in the first step, at least a deformable auxiliary membrane forming an interface between a central portion receiving the cells or tissues to be grown and a rear portion supplied with gas is provided on the opposite side to the second portion, in the first portion of the culture chamber, and in that in the second step, said rear portion is fed according to pressures, flow rates and times depending on said criteria, in order to vary the shape of the auxiliary membrane together with that of each membrane during the culture period, so to generate culture fluid flow.

53. A method according to claim 51, wherein in the first step, the second portion and the pocket or rear portion are supplied with the same selected gas.

54. A method according to claim 48, wherein in the first step, every membrane and the pocket or auxiliary membrane are of a porous material, at least in the direction pointing towards the first portion, so that the selected gas, fed into the second portion and/or the pocket or auxiliary membrane, may at least partially penetrate said first portion.

55. A method according to claim 47, wherein the second step is able to ensure movement of fluid and/or cells and tissues so as to generate in the culture chamber areas where the cell concentrations are different from one another.

56. A method according to claim 55, wherein in the second step, differences in cell concentrations occur by local changes in the first portion's culture volume.

57. A method according to claim 55, wherein in the second step, differences in cell concentrations are obtained through different initial cell concentrations in said culture areas and/or, membrane and/or pocket deformation cycles which differ from one area to the other.

58. A method according to claim 47, wherein the second step is able to ensure together a control over the pressure and flow of the culture fluid in the first portion of the chamber.

59. A method according to claim 53, wherein in the first step at least one partition is provided in the first portion which define culture cavities each extending from a group of membranes to a group of auxiliary membranes, and each able to be supplied with culture fluid and to receive adhering cells as well as culture supports and/or non adhering cells and/or tissues that may differ from one cavity to another.

* * * * *